(12) United States Patent
Cope et al.

(10) Patent No.: US 7,915,006 B2
(45) Date of Patent: Mar. 29, 2011

(54) METHODOLOGIES, PROCESSES AND AUTOMATED DEVICES FOR THE ORIENTATION, SAMPLING AND COLLECTION OF SEED TISSUES FROM INDIVIDUAL SEED

(75) Inventors: Jason Cope, Ankeny, IA (US); David Kurth, Grimes, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 400 days.

(21) Appl. No.: 11/939,402

(22) Filed: Nov. 13, 2007

(65) Prior Publication Data

US 2008/0131924 A1 Jun. 5, 2008

Related U.S. Application Data

(60) Provisional application No. 60/865,563, filed on Nov. 13, 2006, provisional application No. 60/865,554, filed on Nov. 13, 2006.

(51) Int. Cl.
*C12Q 1/08* (2006.01)

(52) U.S. Cl. ........................................................ 435/40

(58) Field of Classification Search ...................... 435/40
See application file for complete search history.

(56) References Cited

U.S. PATENT DOCUMENTS

| | | | |
|---|---|---|---|
| 2,675,942 A | 4/1954 | Vogelsang | |
| 2,875,942 A | 3/1959 | Wilson | |
| 3,344,769 A | 10/1967 | Williams | |
| 3,460,492 A * | 8/1969 | Dickinson et al. | 111/200 |
| 3,636,486 A | 1/1972 | Ioffe et al. | |
| 3,741,793 A | 6/1973 | Simmons | |
| 3,830,902 A | 8/1974 | Barnes | |
| 3,831,736 A | 8/1974 | Barnes | |
| 3,884,347 A | 5/1975 | Gallagher et al. | |
| 3,921,459 A | 11/1975 | Willett | |
| 3,930,212 A | 12/1975 | Ioffe et al. | |
| 3,991,704 A | 11/1976 | Hulstein et al. | |
| 4,238,658 A | 12/1980 | Kalnin et al. | |

(Continued)

FOREIGN PATENT DOCUMENTS

DE 196 16 216 A1 10/1997

(Continued)

OTHER PUBLICATIONS

International Search Report, Pioneer Hi-Bred International, Inc., PCT/US2007/084583, Feb. 10, 2008, 3 Pages.

(Continued)

*Primary Examiner* — Wendy Haas
(74) *Attorney, Agent, or Firm* — Alston & Bird LLP

(57) ABSTRACT

Apparatus, methods, and systems for high throughput, useful sampling of seed, wherein viability is optionally maintained, are disclosed. Seed from one generation in a plant advancement experiment is individually sampled by removal and collection of tissue from the seed. The tissue is then processed to derive one or more biochemical, genetic, or phenotypic characteristic of the seed before a decision is made whether to utilize that seed further in a plant advancement experiment or other plant research and development. In some embodiments of the method, the sampling is controlled to remove a useful amount of tissue for analytical purposes without significant effect on viability potential of the sampled seed. In some embodiments, the sampling is controlled to deter contamination of the sample. In some embodiments, the seed is automatically positioned and oriented to facilitate efficient and accurate sampling.

17 Claims, 21 Drawing Sheets

U.S. PATENT DOCUMENTS

| | | | |
|---|---|---|---|
| 4,278,625 A | 7/1981 | Dedolph | |
| 4,300,462 A | 11/1981 | Wilkins et al. | |
| 5,097,625 A | 3/1992 | Kaneko et al. | |
| 6,409,007 B1 | 6/2002 | Malon | |
| 6,659,338 B1 | 12/2003 | Dittmann et al. | |
| 7,024,817 B2 | 4/2006 | Zehner et al. | |
| 7,043,070 B2 | 5/2006 | Viella | |
| 7,197,374 B2 | 3/2007 | Silverbrook et al. | |
| 7,207,485 B2 | 4/2007 | Silverbrook et al. | |
| 7,502,113 B2 | 3/2009 | Deppermann et al. | |
| 2005/0210744 A1 | 9/2005 | Watanabe et al. | |
| 2006/0042527 A1 | 3/2006 | Deppermann | |
| 2006/0046244 A1 | 3/2006 | Deppermann | |
| 2006/0046264 A1 | 3/2006 | Deppermann et al. | |
| 2006/0048248 A1 | 3/2006 | Deppermann | |
| 2007/0204366 A1 | 8/2007 | Deppermann et al. | |
| 2007/0207485 A1 | 9/2007 | Deppermann et al. | |

FOREIGN PATENT DOCUMENTS

| | | |
|---|---|---|
| EP | 0 611 604 | 8/1994 |
| EP | 1 126 268 A1 | 8/2001 |
| GB | 2 293 744 A | 4/1996 |
| WO | WO 03/100381 A1 | 12/2003 |
| WO | 2007103769 A2 | 9/2007 |
| WO | 2007103786 A2 | 9/2007 |

OTHER PUBLICATIONS

Sangtong, V., et al, "Serial Extraction of Endosperm Drillings (SEED)—A Method for Detecting Transgenes and Proteins in Single Viable Maize Kernels", Plant Molecular Biology Reporter 19:151-158 (Jun. 2001).

John W. K. Leung and K. K. Lai; *Performance analysis of automatic assembly systems with in-line parallel stations*; IMA Journal of Mathematics Applied in Business & Industry; 1997; pp. 1-22; vol. 8, No. 1.

\* cited by examiner

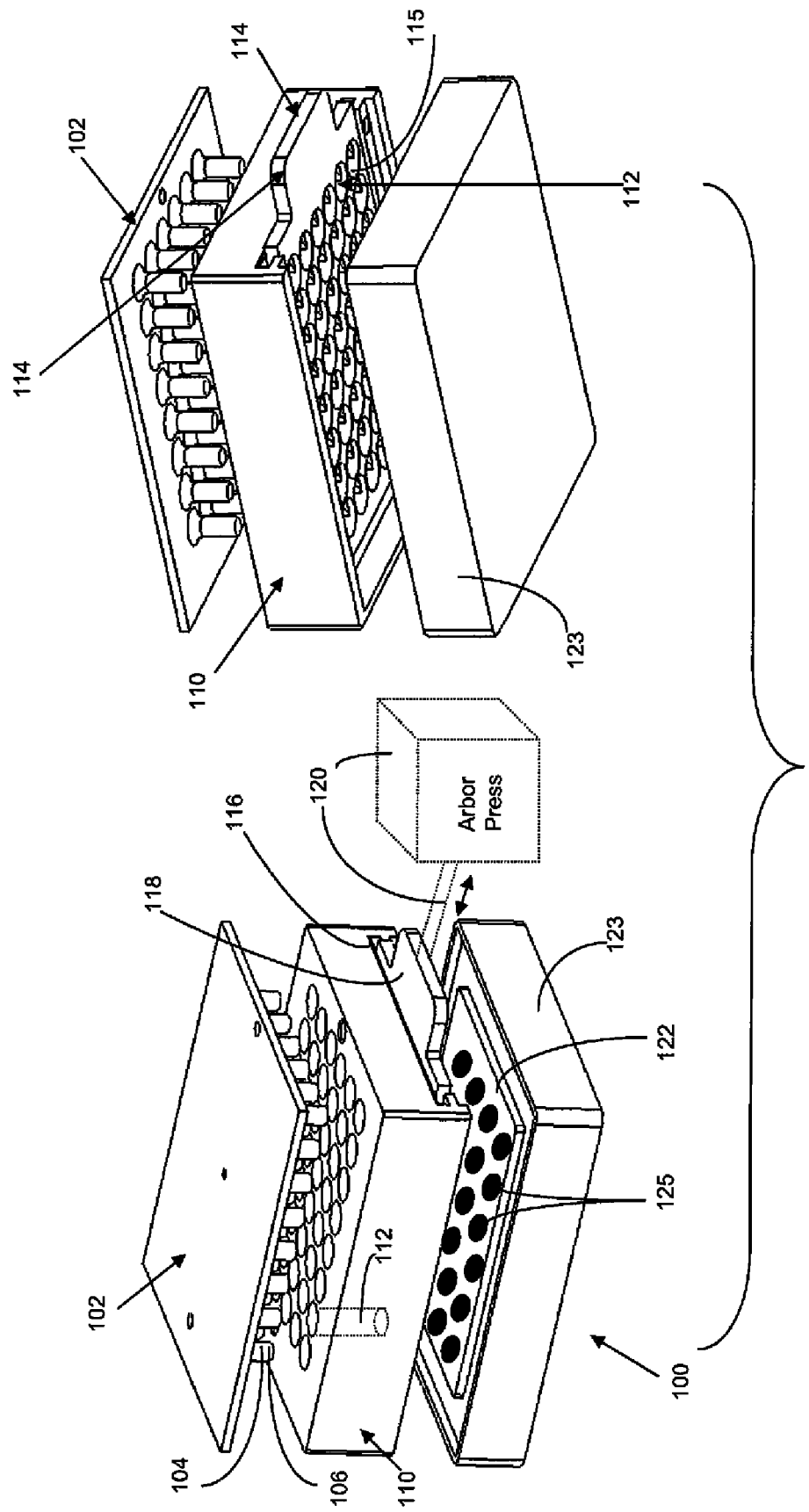

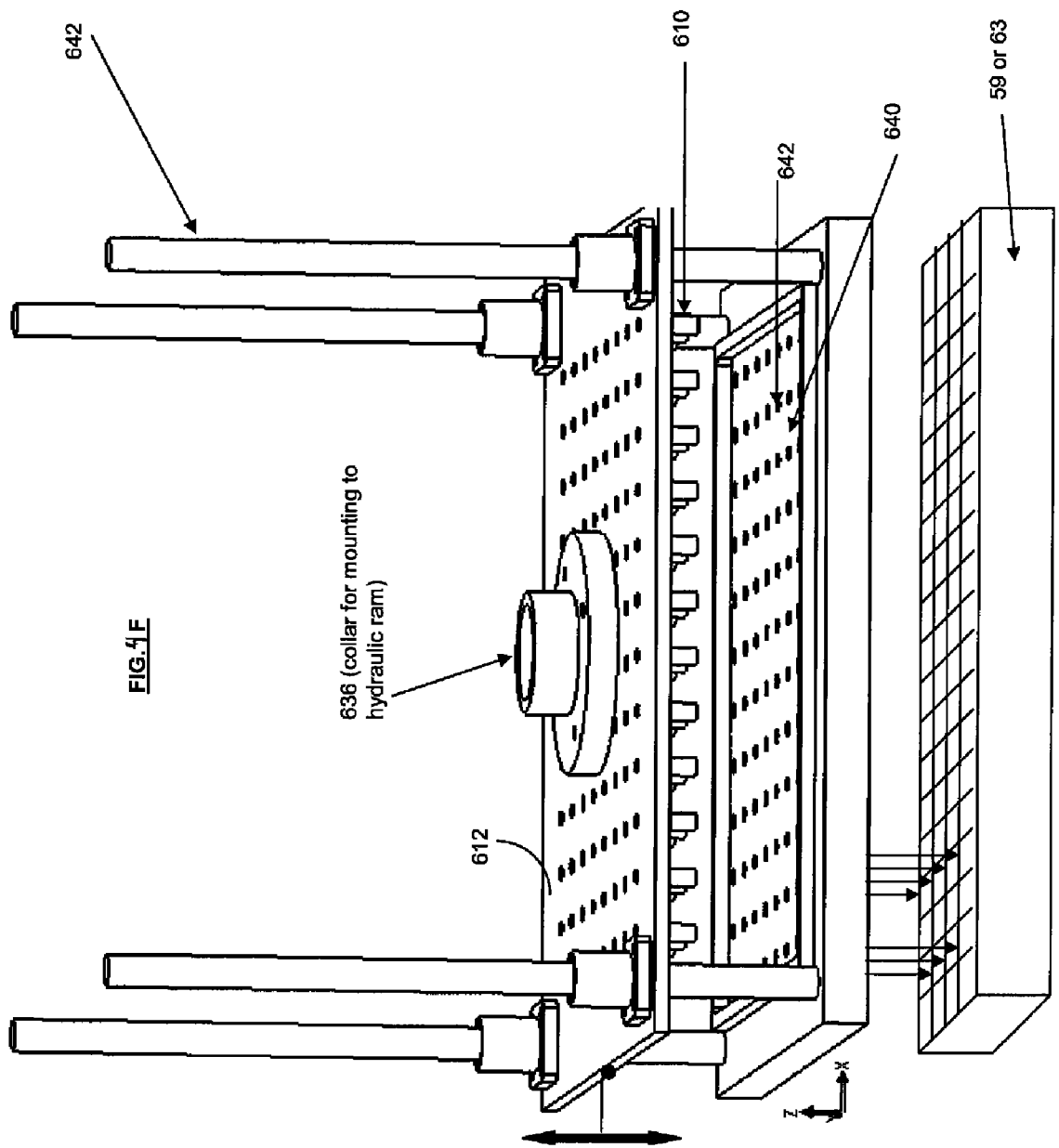

METHODOLOGIES, PROCESSES AND AUTOMATED DEVICES FOR THE ORIENTATION, SAMPLING AND COLLECTION OF SEED TISSUES FROM INDIVIDUAL SEED

CROSS-REFERENCE TO RELATED APPLICATIONS

This application claims priority under 35 U.S.C. §119 of provisional applications U.S. Ser. No. 60/865,554 and U.S. Ser. No. 60/865,563, both filed Nov. 13, 2006, which applications are hereby incorporated by reference in their entireties.

I. BACKGROUND OF THE INVENTION

A. Field of the Invention

The present invention relates to obtaining tissue samples from individual seed in an efficient way.

B. Problems in the Art

It is conventional practice in plant breeding or plant advancement experiments to grow plants from seed of known parentage. The seed are planted in experimental plots, growth chambers, greenhouses, or other growing conditions in which they are either cross pollinated with other plants of known parentage or self pollinated. The resulting seed are the offspring of the two parent plants or the self pollinated plant, and are harvested, processed and planted to continue the plant breeding cycle. Specific laboratory or field-based tests may be performed on the plants, plant tissues, seed or seed tissues, in order to aid in the breeding or advancement selection process.

Generations of plants based on known crosses or self pollinations are planted and then tested to see if these lines or varieties are moving towards characteristics that are desirable in the marketplace. Examples of desirable traits include, but are not limited to, increased yield, increased homozygosity, improved or newly conferred resistance and/or tolerance to specific herbicides and/or pests and pathogens, increased oil content, altered starch content, nutraceutical composition, drought tolerance, and specific morphological based trait enhancements.

As can be appreciated and as is well known in the art, these experiments can be massive in scale. They involve a huge labor force ranging from scientists to field staff to design, plant, maintain, and conduct the experiments, which can involve thousands or tens of thousands of individual plants. They also require substantial land resources. Plots or greenhouses can take up thousands of acres of land. Not only does this tie up large amounts of land for months while the plants germinate, grow, and produce seed, during which time they may be sampled for laboratory or field testing, but then the massive amounts of seed must be individually tagged, harvested and processed.

A further complication is that much of the experimentation goes for naught. It has been reported in the literature that some seed companies discard 80-90% of the plants in any generation early on in the experiment. Thus, much of the land, labor and material resources expended for growing, harvesting, and post-harvest processing ultimately are wasted for a large percentage of the seed.

Timing pressures are also a factor. Significant advances in plant breeding have put more pressure on seed companies to more quickly advance lines or varieties of plants for more and better traits and characteristics. The plant breeders and associated workers are thus under increasing pressure to more efficiently and effectively process these generations and to make more and earlier selections of plants which should be continued into the next generation of breeding.

Therefore, a movement towards earlier identification of traits of interest through laboratory based seed testing has emerged. Seed is non-destructively tested to derive genetic, biochemical or phenotypic information. If traits of interest are identified, the selected seed from specific plants are used either for further experiments and advancement, or to produce commercial quantities. Testing seed prevents the need to grow the seed into immature plants, which are then tested. This saves time, space, and effort. If effective, early identification of desirable traits in seed can lead to greatly reducing the amount of land needed for experimental testing, the amount of seed that must be tested, and the amount of time needed to derive the information needed to advance the experiments. For example, instead of thousands of acres of plantings and the subsequent handling and processing of all those plants, a fraction of acres and plants might be enough. However, because timing is still important, this is still a substantial task because even such a reduction involves processing, for example, thousands of seed per day.

A conventional method of attempting non-lethal seed sampling is as follows. A single seed of interest is held with pliers above a sheet of paper laid out on a surface. A small drill bit is used to drill into a small location on the seed. Debris removed by the drill bit from the seed is collected of the sheet of paper. The paper is lifted and the debris is transferred to a test tube or other container. It is thus collected and ready for laboratory analysis. This method is intended to be non-lethal to the seed. However, the process is slow. Its success and effectiveness depends heavily on the attention and accuracy of the worker. Each single seed must be manually picked up and held by the pliers. The drilling is also manual. Care must be taken with the drilling and the handling of the debris. Single containers, e.g. the individual test tubes, must then be handled and marked or otherwise tracked and identified. Additionally, the pliers and drill must be cleaned between the sampling of each seed. There can be substantial risk of contamination by carry-over from sample to sample and the manual handling. Also, many times it is desirable to obtain seed material from a certain physiological tissue of the seed. For example, with corn seed, it may be desirable to take the sample from the endosperm. It such cases, it is not trivial, but rather is time-consuming and somewhat difficult, to manually grasp a small corn seed is such a way to allow the endosperm to be oriented to expose it for drilling. Sampling from other seed structures such as the seed germ must be avoided because sampling from such regions of the seed negatively impacts germination rates. Sometimes it is difficult to obtain a useful amount of sample with this method. In summary, sampling from seed relies heavily on the skill of the worker and is relative to throughput and accuracy, including whether the procedure gives the seed a good chance at germination. These issues are amplified when a worker is charged with processing many seed a day.

Another example of non-lethally obtaining tissue samples from corn seed for laboratory analysis is disclosed at V. Sangtong, E. C. Mottel, M. J. Long, M. Lee, and M. P. Scott, *Serial Extraction of Endosperm Drillings (SEED)—A Method for Detecting Transgenes and Proteins in Single Viable Maize Kernels*, Plant Molecular Biology Reporter 19: 151-158, June 2001, which is incorporated by reference herein. It describes use of a hand-held rotary grinder to grind off particles, called "drillings," from the kernel and collection of the particles to test for the presence of certain genes. However, this method also requires manual grasping and orientation of each individual seed relative to the grinder. It, too is time consuming and somewhat cumbersome. It also relies on the skill of the worker. This method raises issues of throughput, accuracy, whether a useful amount of sample is obtained, and contamination. The grinder must be thoroughly cleaned between each sample in order to prevent contamination.

As evidenced by these examples, present conventional seed analysis methods, such as is used in genetic, biochemical, or phenotypic analysis, require at least a part of the seed to be removed and processed. In removing some seed tissue, various objectives may need to be met. These may include one or more of the following objectives:

(a) maintain seed viability post-sampling if required.

(b) obtain at least a minimum required sample amount, without affecting viability.

(c) obtain a sample from a specific location on the seed, often requiring the ability to orient the seed in a specific position for sampling.

(d) maintain a particular throughput level for efficiency purposes.

(e) reduce or virtually eliminate contamination between samples.

(f) allow for the tracking of separate samples and their correlation to other samples in a group.

(a) Viability

With regard to maintaining seed viability, it may be critical in some circumstances that the seed sampling method and apparatus not damage the seed in such a way that seed viability is reduced. It is often desirable that such analysis be non-lethal to the seed, or at least result in a substantial probability that the sampled seed will germinate (e.g. no significant decrease in germination potential) so that it can be grown into a mature plant. For some analyses, seed viability does not need to be maintained, in which case larger samples can often be taken. The need for seed viability will depend on the intended use of the seeds post-sampling.

(b) Sample Amount

It is desirable to obtain a useful amount of sample. To be useful, in some applications it must be above a certain minimum amount necessary in order to perform a given test and obtain a meaningful result. Different tests or assays require different sample amounts. It may be equally important to avoid taking too much tissue for a sample, because a sample that is too large may reduce germination potential of a seed, which may be undesirable. Therefore, it is desirable that sampling apparatus and methods allow for variation in the amount of sample taken from any given seed.

(c) Sample Location

A useful sample amount also can involve sample location accuracy. For example, in some applications the sample must come only from a certain location or from certain tissue. Further, it is difficult to handle small particles like many seed. It is also difficult to accurately position and orient seed. On a corn seed, for example, it may be important to sample the endosperm tissue, and orient the corn seed for sampling that particular tissue. Therefore, it is desirable that sampling apparatus and methods are adapted to allow for location-specific sampling, which may include specific seed orientation methods.

(d) Throughput

A sampling apparatus and methodology must consider the throughput level that supports the required number of samples being taken in a time efficient manner. For example, some situations involve the potential need to sample thousands, hundreds of thousands, or even millions of seed per year. Taking the hypothetical example of a million seed per year, and a 5-day work week, this would average nearly four thousand samples per day for each working day of a year. It is difficult to meet such demand with lower throughput sampling methods. Accordingly, higher throughput, automatic or even semi-automatic methods may be desirable.

(e) Avoiding Contamination

It is desirable that a sampling methodology and apparatus not be prone to cross-contamination in order to maintain sample purities for subsequent analytical testing procedures. This can involve not only sample location accuracy, such that a sample from a given location is not contaminated with tissue from a different location, but also the method of sampling and the handling of each individual sample, ensuring no contamination between samples.

(f) Tracking Samples

Efficient processing of seed and samples removed from seed presents a variety of issues and challenges, especially when it is important to keep track of each seed, each sample, and their correlation to each other, or to other samples within a bath. Accordingly, it is desirable that a sampling apparatus and methodology allow for easy tracking of seed and samples.

Conventional seed sampling technologies do not address these requirements sufficiently, resulting in pressures on capital and labor resources, and thus illustrate the need for an improvement in the state of the art. The current methods are relatively low throughput, have substantial risk of cross-contamination, and tend to be inconsistent because of a reliance on significant manual handling, orienting, and removal of the sample from the seed. This can affect the type of sample taken from the seed and the likelihood that the seed will germinate. There is a need to eliminate the resources current methods require for cleaning between samples. There is a need to reduce or minimize cross-contamination between samples by carry-over or other reasons, or any contamination from any source of any sample. There is also a need for more reliability and accuracy. Accordingly, there is a need for methodologies and their corresponding apparatus which provide for seed sampling that accomplishes one or more of the following objectives:

(a) maintains seed viability post-sampling;

(b) obtains at least a minimum required sample amount, without affecting viability;

(c) obtains a sample from a specific location on the seed;

(d) maintains a particular throughput level for efficiency purposes;

(e) reduces or virtually eliminate contamination between samples; and (f) allows for the tracking of separate samples and their correlation to other samples in a group.

Some of these objectives that are desirable when sampling seed can be conflicting and even antagonistic. For example, obtaining a useful sample amount while maintaining seed viability requires taking some seed tissue, but not too much tissue. High throughput methodologies may require relatively rapid operation but with relatively high accuracy and low contamination risk, such that they must be done more slowly than is technically possible. These multiple objectives have therefore existed in the art and have not been satisfactorily addressed or balanced by the currently available methods and apparatuses. There is a need in the art to overcome the above-described types of problems such that the maximum number of objectives is realized in any given embodiment. It is recognized that not all objectives can always be realized in all embodiments of a given sampling method or apparatus.

II. SUMMARY OF THE INVENTION

It is therefore an embodiment of the present invention to provide an apparatus, method, or system which improves over the problems and deficiencies in the state of the art.

Further embodiments of the present invention include an apparatus, method, or system which:
 a. promotes higher through-put of collecting samples from plural individual seed;
 b. provides rapid acquisition of samples;
 c. promotes sampling with relatively high germination rates for the sampled seed;
 d. promotes relatively consistent, accurately measured samples of useful amounts;
 e. provides for efficient biochemical, genetic, or phenotypic evaluation of samples;
 f. promotes more efficient selection during a plant advancement experiment;
 g. avoids contamination of samples and cross-contamination between samples;
 h. minimizes cleaning requirements;
 i. promotes sampling which is not detrimental to biochemical, genetic, or phenotypic testing;
 j. promotes sampling which is not detrimental to the plant grown from the sampled seed, or the soil or environment around the plant;
 k. promotes accuracy, consistency and reliability of sampling;
 l. promotes automation of sampling for biochemical, genetic, or phenotypic analysis of the samples;
 m. can include automatic seed orientation to promote accurate and consistent sampling of a particular part of each seed;
 n. is flexible in application to a variety of seed types and a variety of sampling tasks;
 o. is efficient and robust;
 p. is highly repeatable;
 q. can reduce the amount of field space and the number of samples that are needed for analysis and for shipping in plant advancement experiments;
 r. reduces materials required for management of plant nurseries; and/or
 s. reduces overall labor resource requirements;
 t. reduces plant tracking and tagging efforts;
 u. improves ergonomics of the sampling process.

One embodiment of the present invention is a method whereby seed from one generation in a plant advancement experiment is individually sampled by removal and collection of a useful amount of tissue from the seed without significant reduction in germination potential or viability of the sampled seed. The tissue is then processed to derive one or more biochemical, genetic, or phenotypic characteristics of the seed before a decision is made whether to utilize that seed further in the plant advancement experiment. This allows a decision to be made as soon as the seed matures in a given generation, as opposed to harvesting the seed, planting it in an experimental plot, and then testing the immature plant by scientific analyses such as genetic testing for the presence of traits that influence seed components such as oils, proteins, starches, or other such procedures. This allows for earlier determination of which offspring will be selected to continue in the experiment. It further allows the benefit of reducing the amount of land required for experimental plots. In a single nursery it essentially reduces the amount of land required to screen thousands of plants by identifying the 10%-20% of the seed that are needed for advancement. As a result, no field sampling is required because decisions are not based on plant tissue. The seed sampling technique allows for a quick and efficient decision on which seed carry desirable genetic traits or other characteristics Another embodiment of the invention is a method, apparatus, and system for effectively and automatically obtaining samples of useful amounts from seed while maintaining a high germination potential for the seed.

Another embodiment of the invention deters contamination in sample taking and handling.

Another embodiment of the invention utilizes a mechanism or method to automatically position and orient a seed so that an automated sampling of seed tissue can occur consistently, quickly, and effectively. One example utilizes a laser beam to cut or separate the sample from the seed.

A further embodiment of the invention is directed to a particular throughput level for seed sampling. The level can be selected based on a set of factors and/or circumstances regarding the sampling method and apparatus.

Additional embodiments of the present invention comprise a variety of alternative methods and mechanisms for obtaining a seed tissue sample.

Still further embodiments of the present invention comprise methods of maintaining the one-to-one correlation between the seed and the seed tissue sample for selection and recovery purposes. Alternatively, correlations can be maintained between one sample and other samples.

These and other embodiments of the present invention will become apparent with reference to the accompanying specification and claims.

III. BRIEF DESCRIPTION OF THE DRAWINGS

Appended to this description are several drawings and illustrations that will be referred to herein and which are incorporated by reference into this description.

A. Magnetic Orientation and Laser Cutting of Individual Seed

B. Magnetic Orientation and Simultaneous Chopping Portion from Plural Seed and Collecting Chopped Samples FIG. 2A is an illustration of an exemplary embodiment according to another aspect of the present invention which magnetically positions and orients a plurality of seed to allow simultaneous chopping off and collection of a portion of each seed.

Figure 2B:
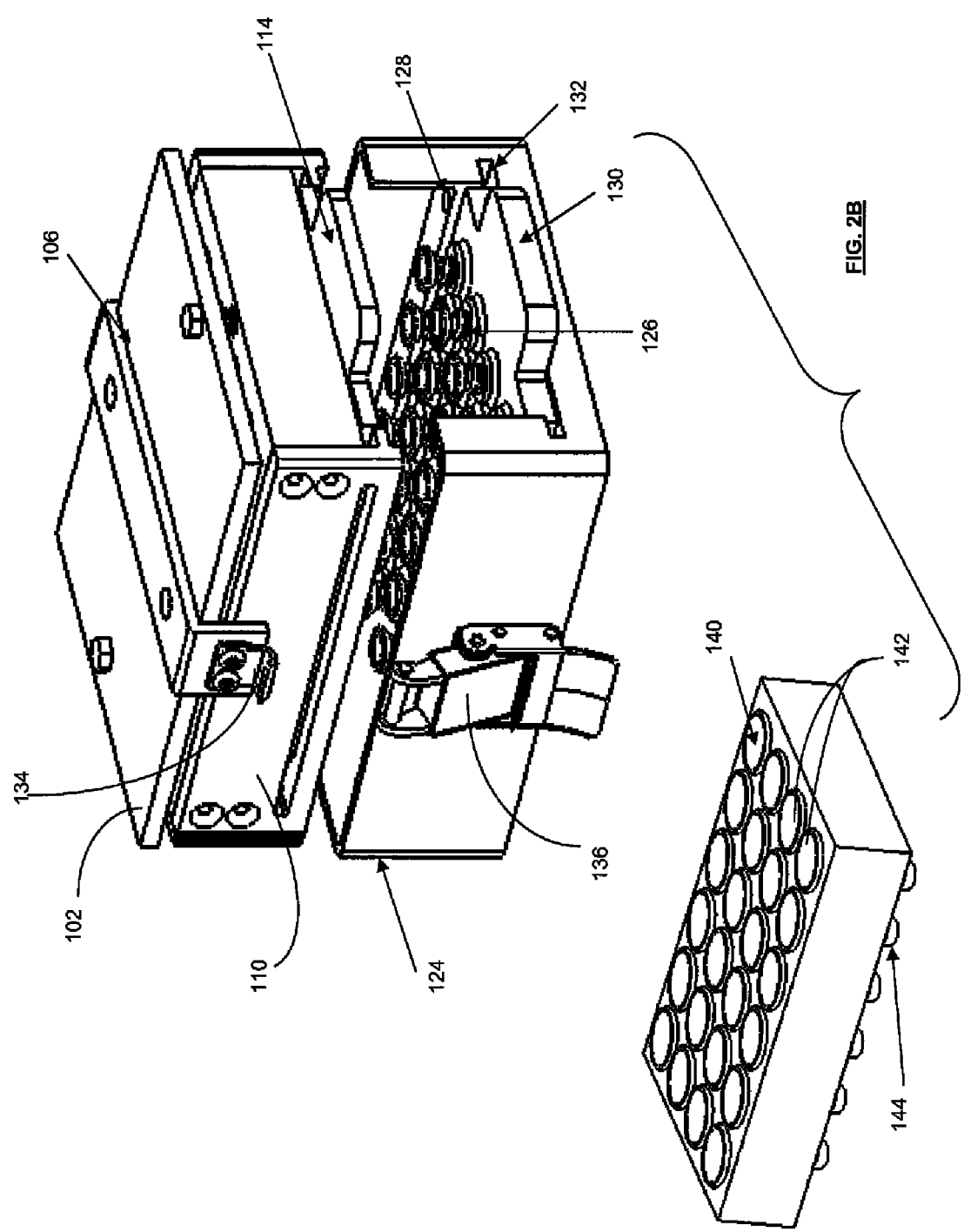

FIG. 2B is an alternative embodiment according to similar principles to the embodiment of FIG. 2A.

Figure 2C:
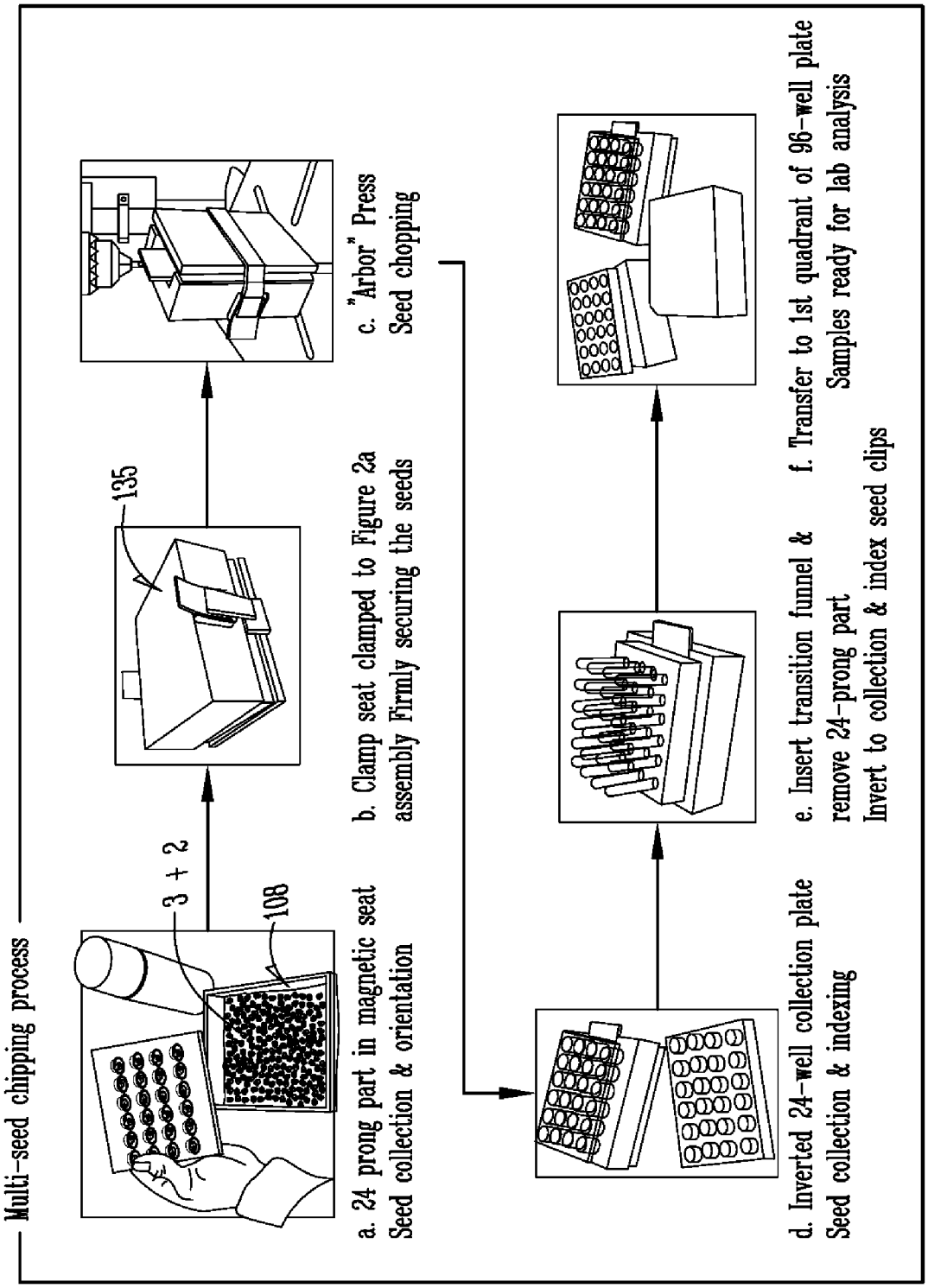

FIG. 2C is an illustration of a method of using the embodiment of FIG. 2B.

Figure 2D:
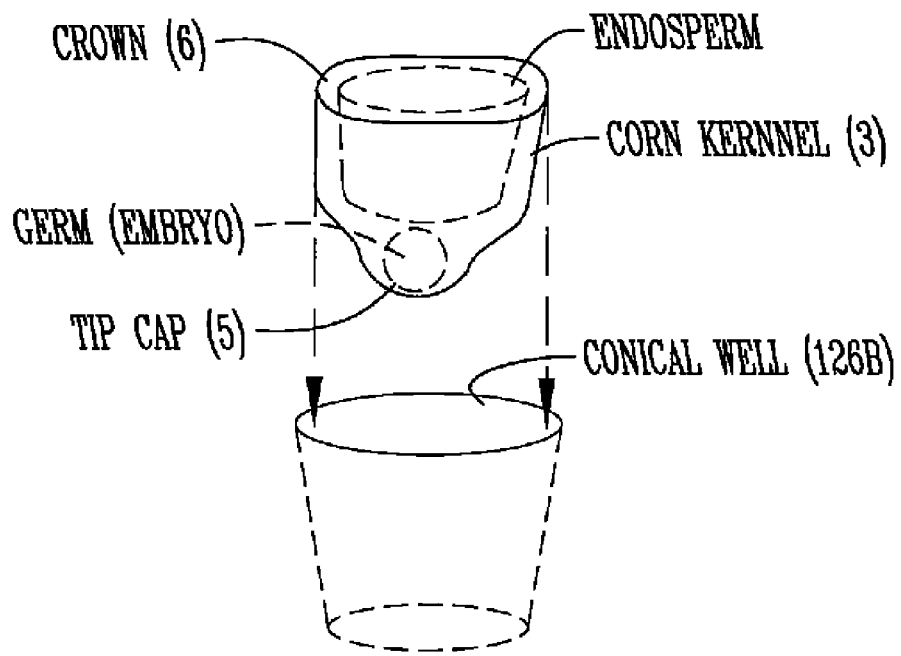

FIGS. 2D and E are enlarged isolated illustrations of an optional tapered well or receiver to position and orient a seed automatically.

C. Drilling Seed and Collecting Debris

Figure 3A:
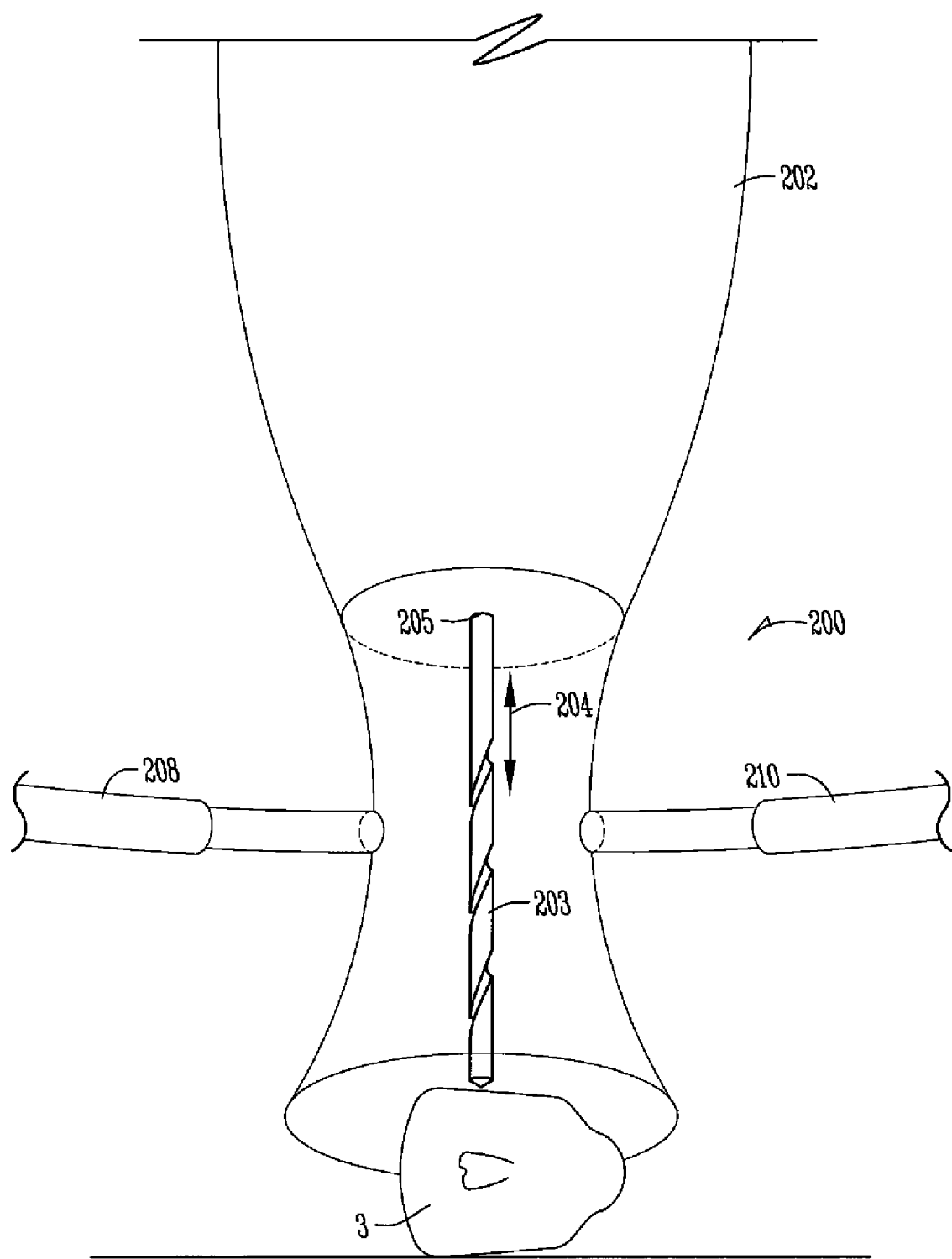

FIG. 3A are illustrations of a drilling tool equipped with air aspiration and air irrigation functions for use in drilling and collecting debris from an individual seed.

Figure 3B:
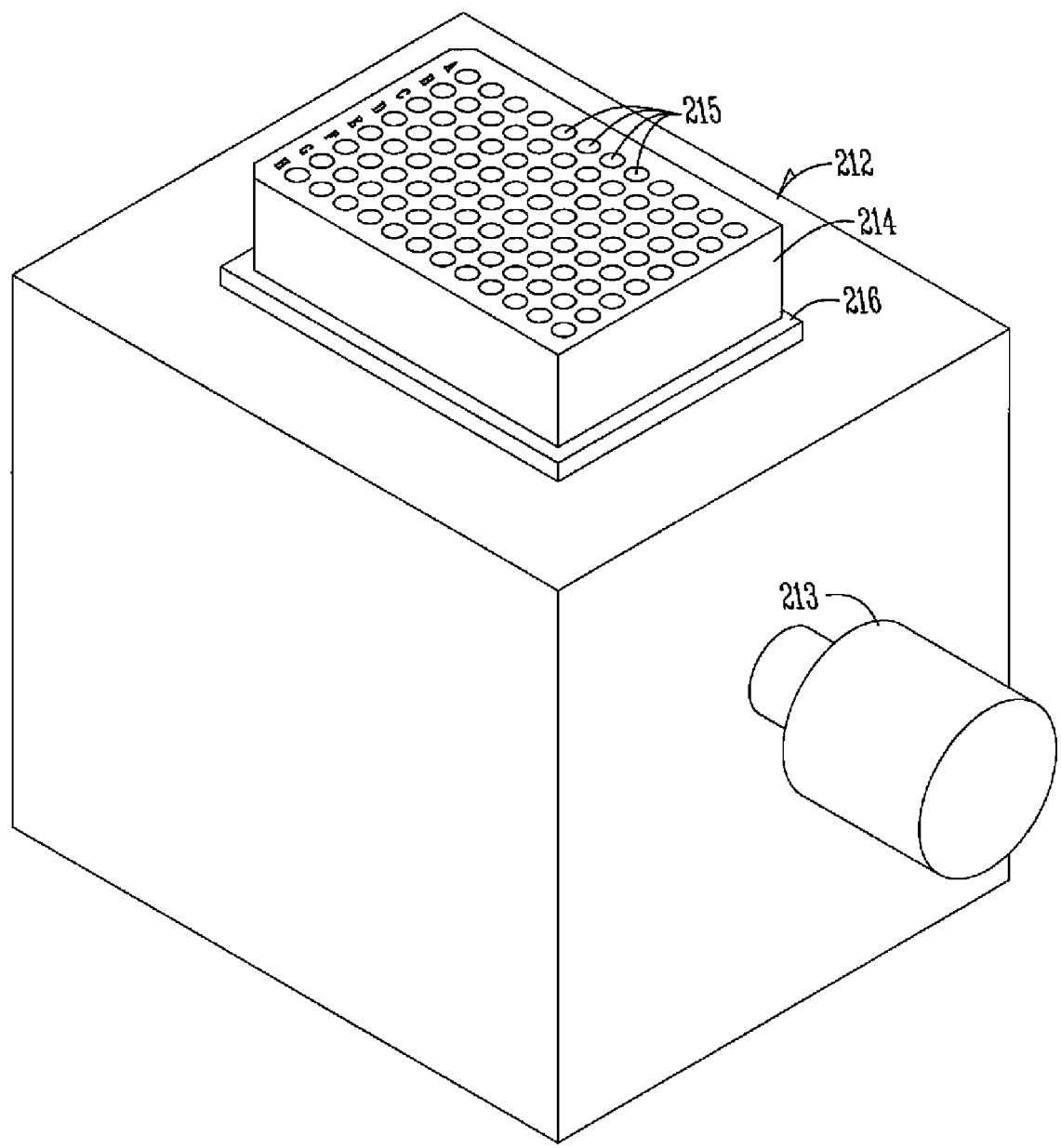
Figure 3C:
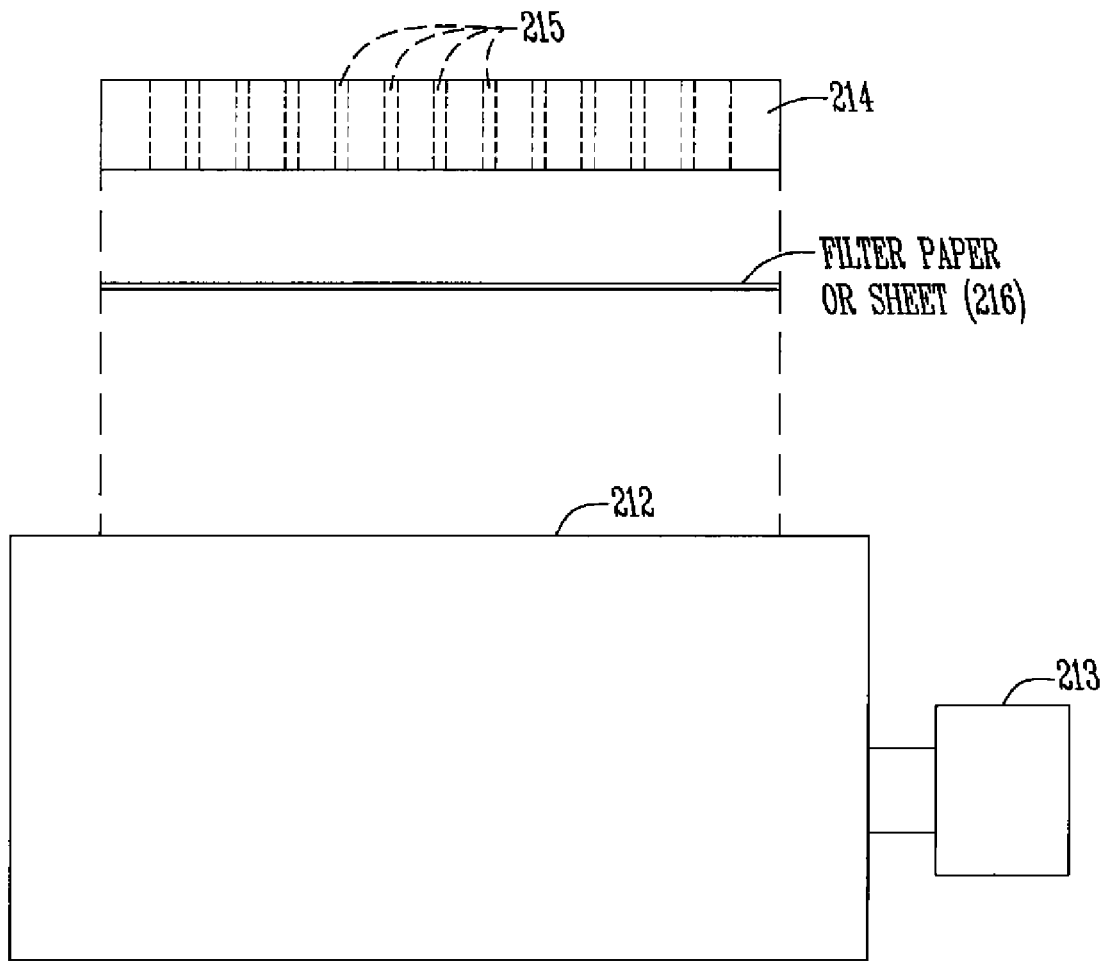
Figure 3D:
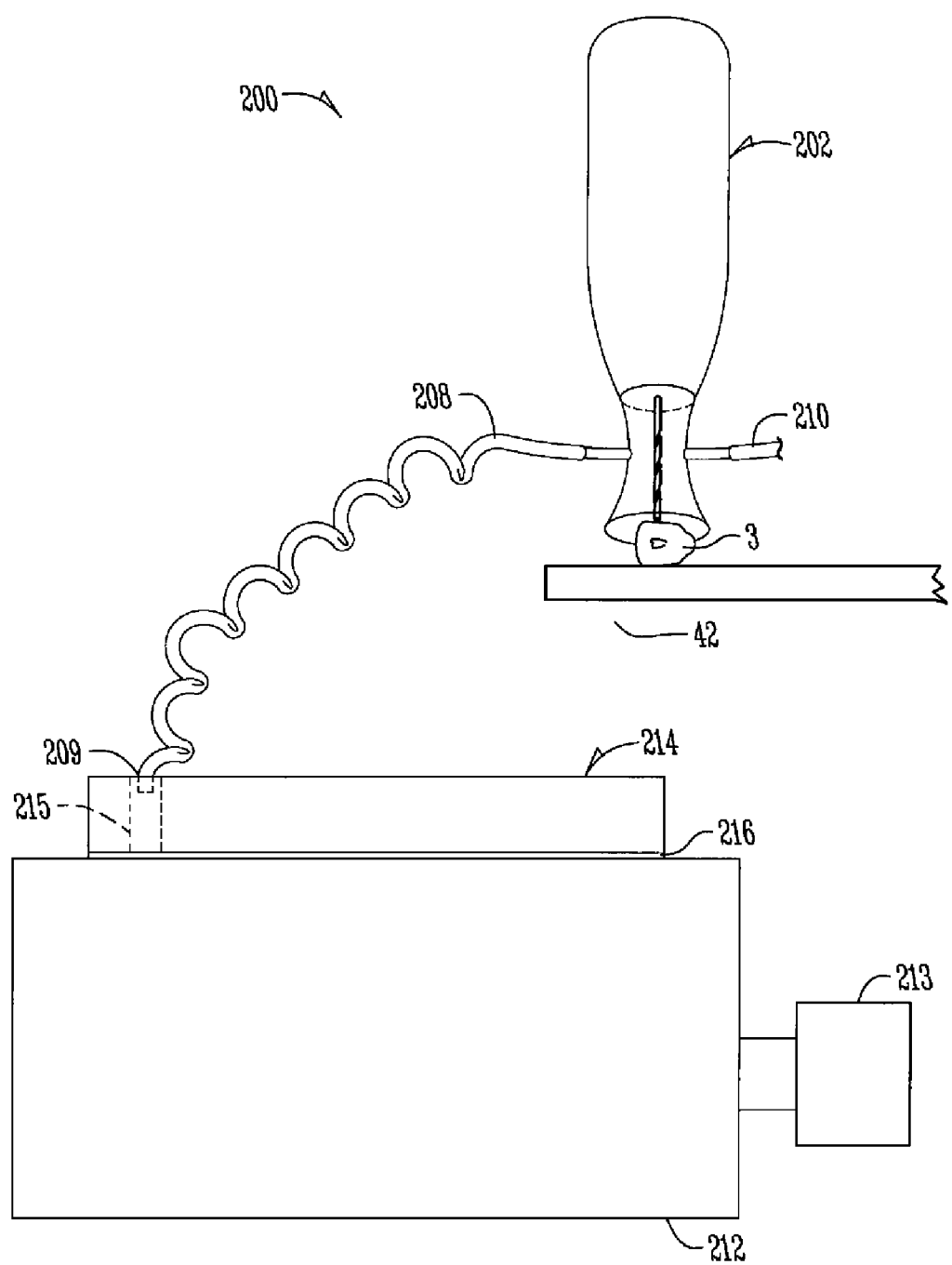

FIGS. 3B-D illustrates a collection plate and vacuum box for use with the drilling tool of FIG. 3A.

Figure 3E:
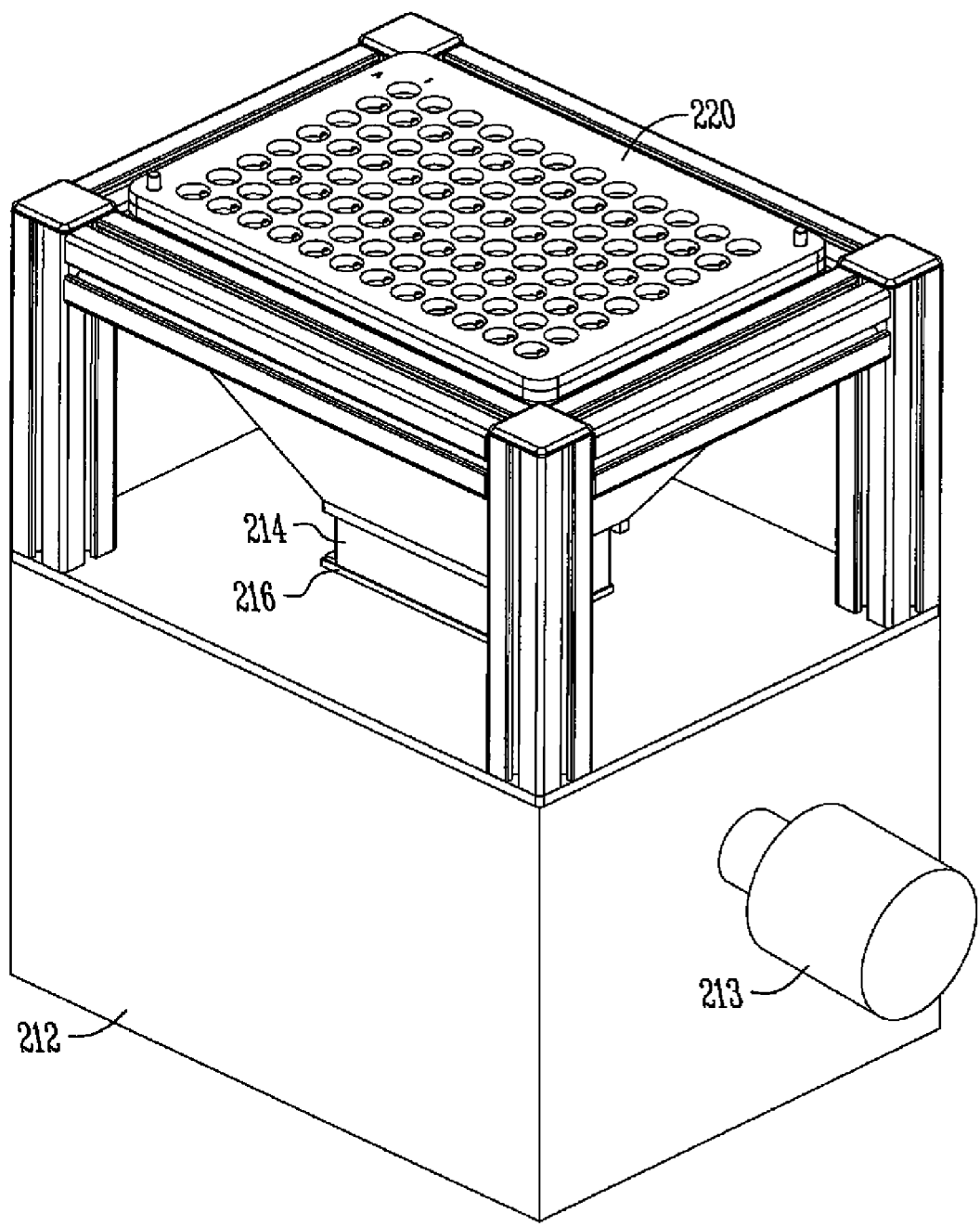

FIGS. 3E and F are illustrations of an alternative embodiment similar to that of FIGS. 3A-D, but which includes a seed positioning plate having multiple seed wells. Each well holds and positions an individual seed and the drilling tool illustrated in FIG. 3A can be inserted sequentially to drill and collect debris into a collection plate.

D. Sand Seed and Collect Sandpaper Punches

Figure 4A:
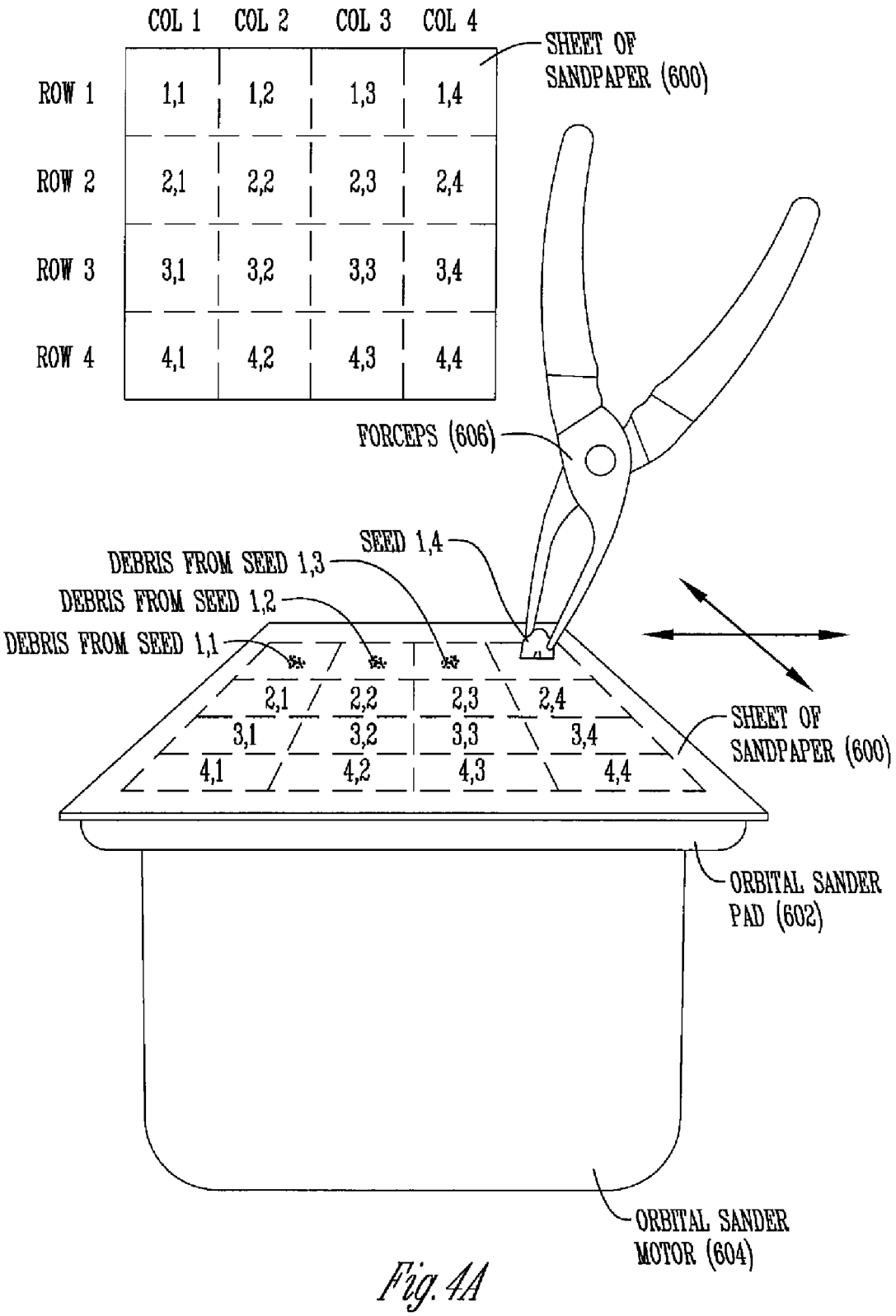
Figure 4B:
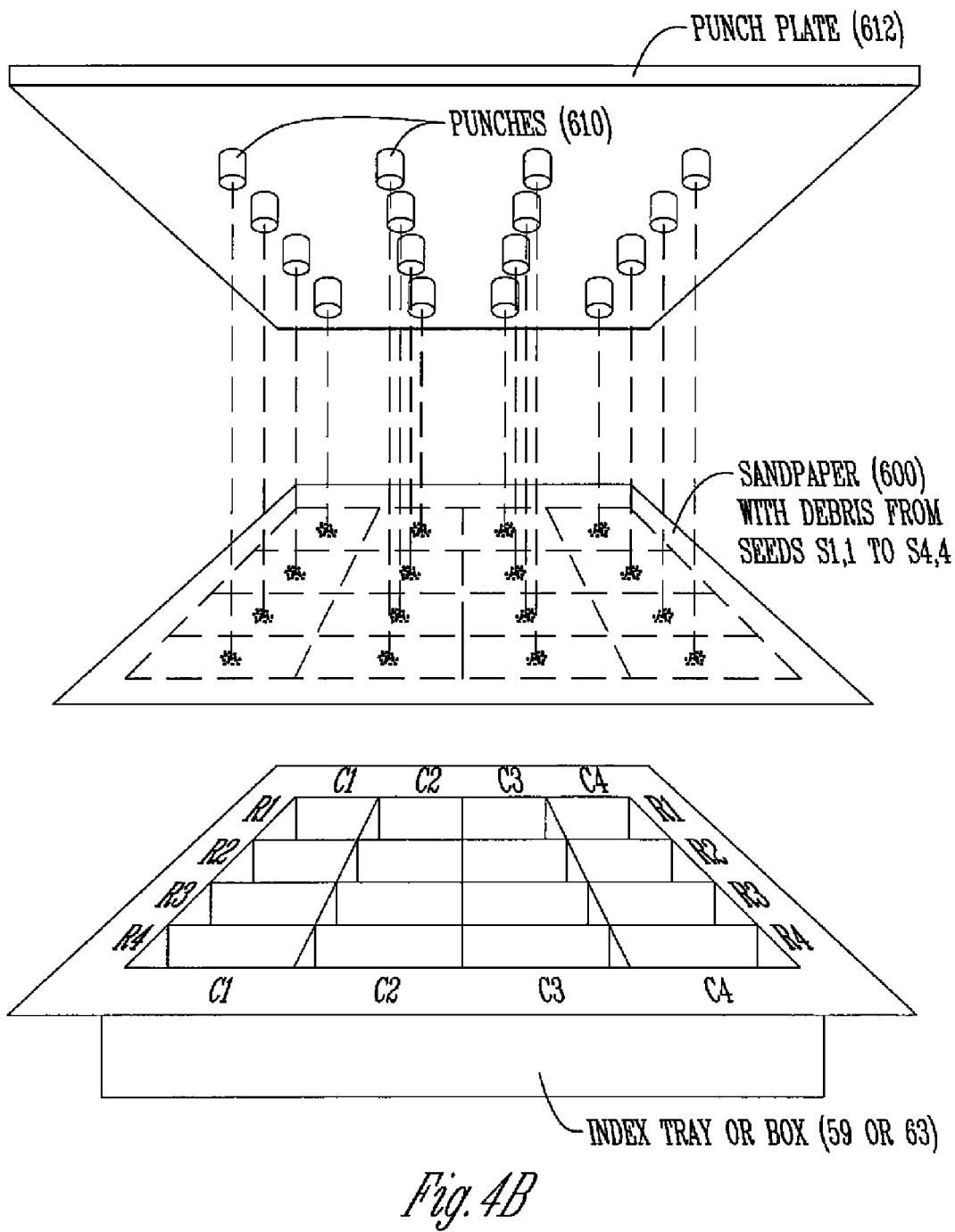
Figure 4C:
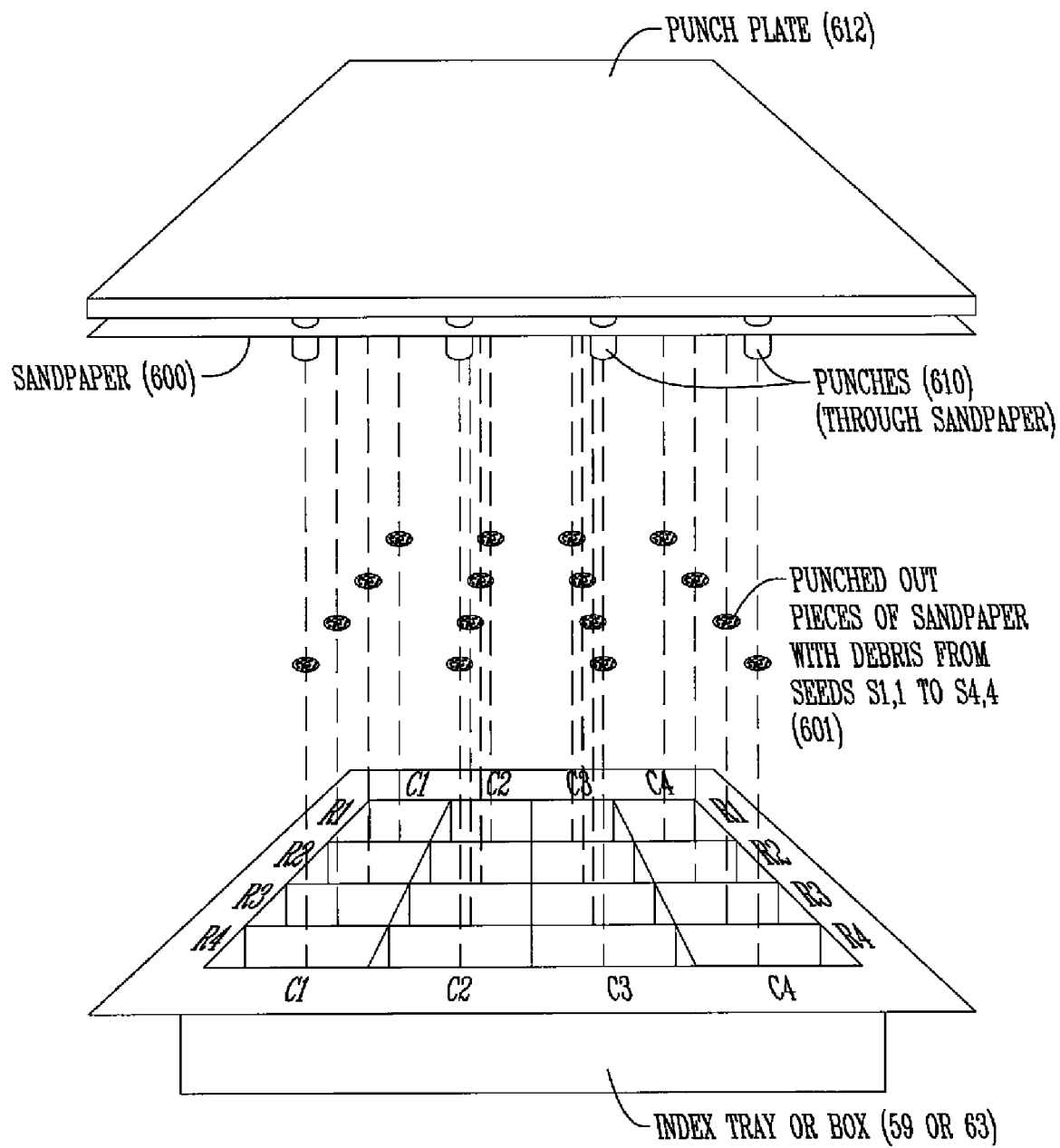

FIGS. 4A-C illustrate diagrammatically another exemplary embodiment according to an aspect of the present invention including a methodology of sanding and collecting the debris from individual seed for further use, namely removing tissue from each seed at a separate location on a sheet of sandpaper and then punching out pieces of the sandpaper at those locations into an index tray or plate.

Figure 4D:
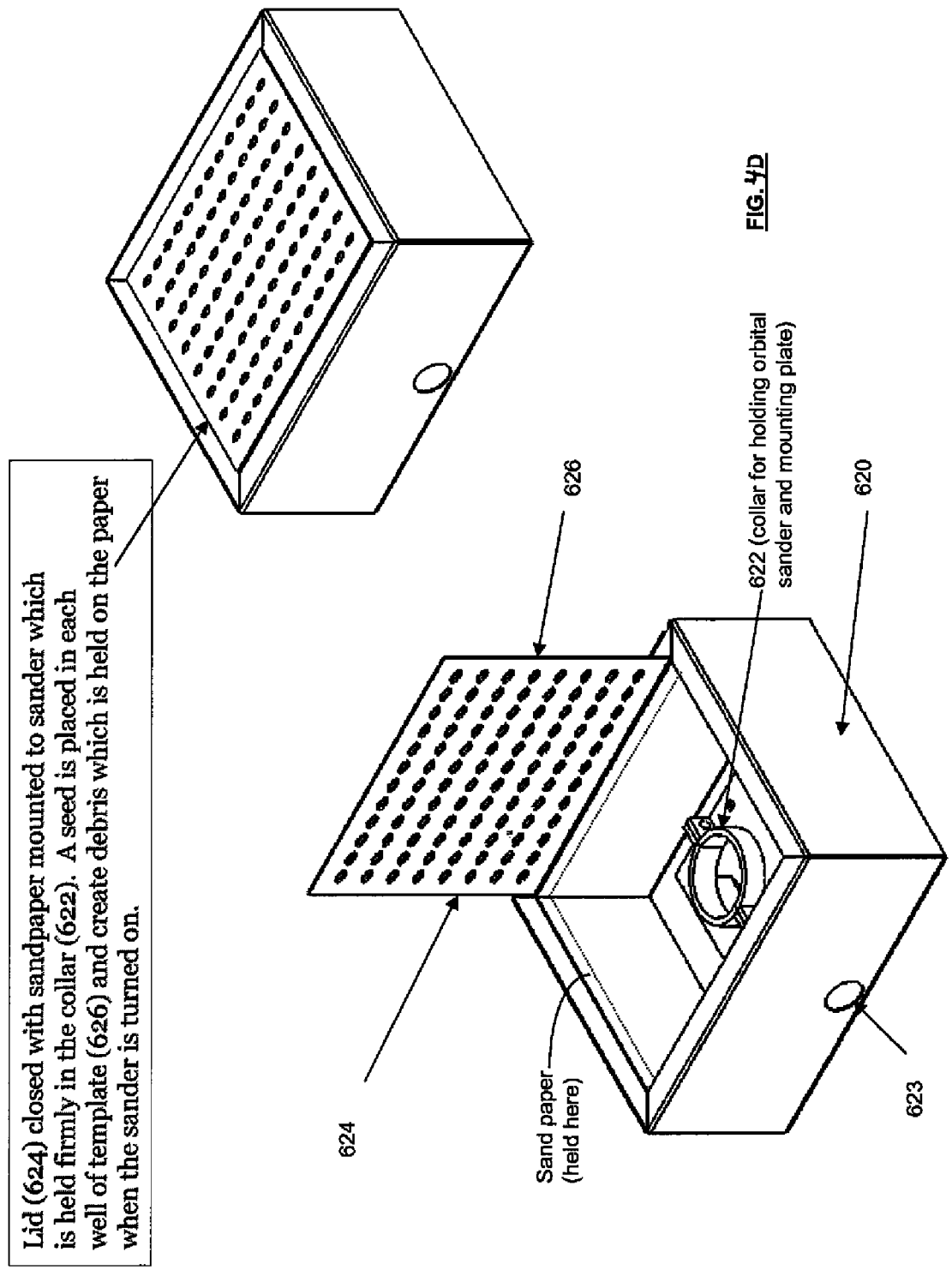

FIG. 4D is perspective views of an apparatus to obtain sanded samples of plural seed simultaneously.

Figure 4E:
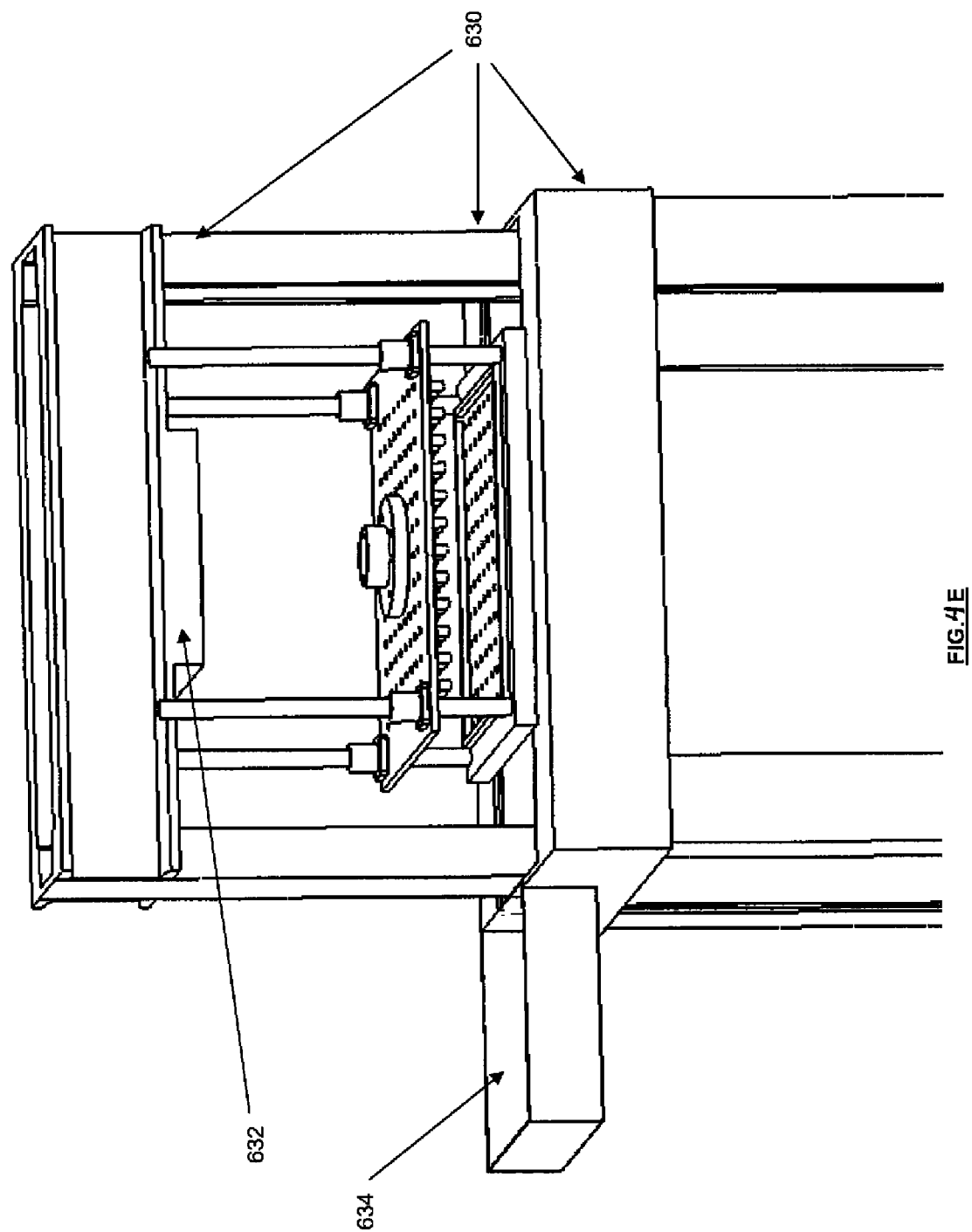

FIG. 4E is a perspective view of a hydraulic punch press that can be used to automatically punch sanded samples and collect them.

FIG. 4F is an enlarged partial perspective of FIG. 4E, including a diagrammatic illustration of a collection or indexing tray for the samples.

IV. DETAILED DESCRIPTION OF EXEMPLARY EMBODIMENTS

A. Overview

For a better understanding of the invention, examples of how aspects of the invention can be practiced will now be described in detail. It is to be understood that these are but several forms the invention can take and do not limit the invention.

Frequent reference will be taken to the accompanying drawings. Reference numerals and/or letters will be used to indicate certain parts and locations throughout the drawings. The same reference numerals will be used to indicate the same parts or locations unless otherwise indicated.

The context of these specific examples will be with respect to kernels of corn. It is to be understood, however, that this example is only intended to illustrate one application of the invention. The invention can be utilized for other seed and other objects. The range of sizes can vary as well as the nature of the object. As will be understood by one of skill in the art, the embodiments of the invention will be used with seed that are of convenient size to be sampled. Some seed are extremely fine and small, somewhat like dust particles or grains of salt, while others are particularly large and hard, such as the seed from the *Lodoicea maldivica* palm, which are 20 to 24 pounds in weight. One of skill in the art recognizes that seed intended to be used with the embodiments of the invention must be of a size and weight that allow convenient sampling with the apparatus of the embodiments. Such seed include, but are not limited to, many agriculturally important seed such as seed from maize (corn), soybean, *Brassica* species, canola, cereals such as wheat, oats or other grains, and various types of vegetable and ornamental seed. Analogous applications will be obvious from this example and variations obvious to those skilled in the art will be included.

Reference will be made to samples taken from a seed. Sampling methods may be referred to in different terms, such as, for example, sampling, chipping, clipping, slicing, cutting, snipping or removing a sample. The sample that has been taken can also be referred to using different terms, such as, for example, seed sample, seed tissue sample, seed chip, seed snip, seed sliver, seed clip or clipping, and seed portion.

B. First Concept

Magnetic Orientation and Sequential Laser Cutting of Successive Individual Seed

1. Embodiment 1 a) Apparatus (FIGS. 1A and 1C)

Figure 1A:
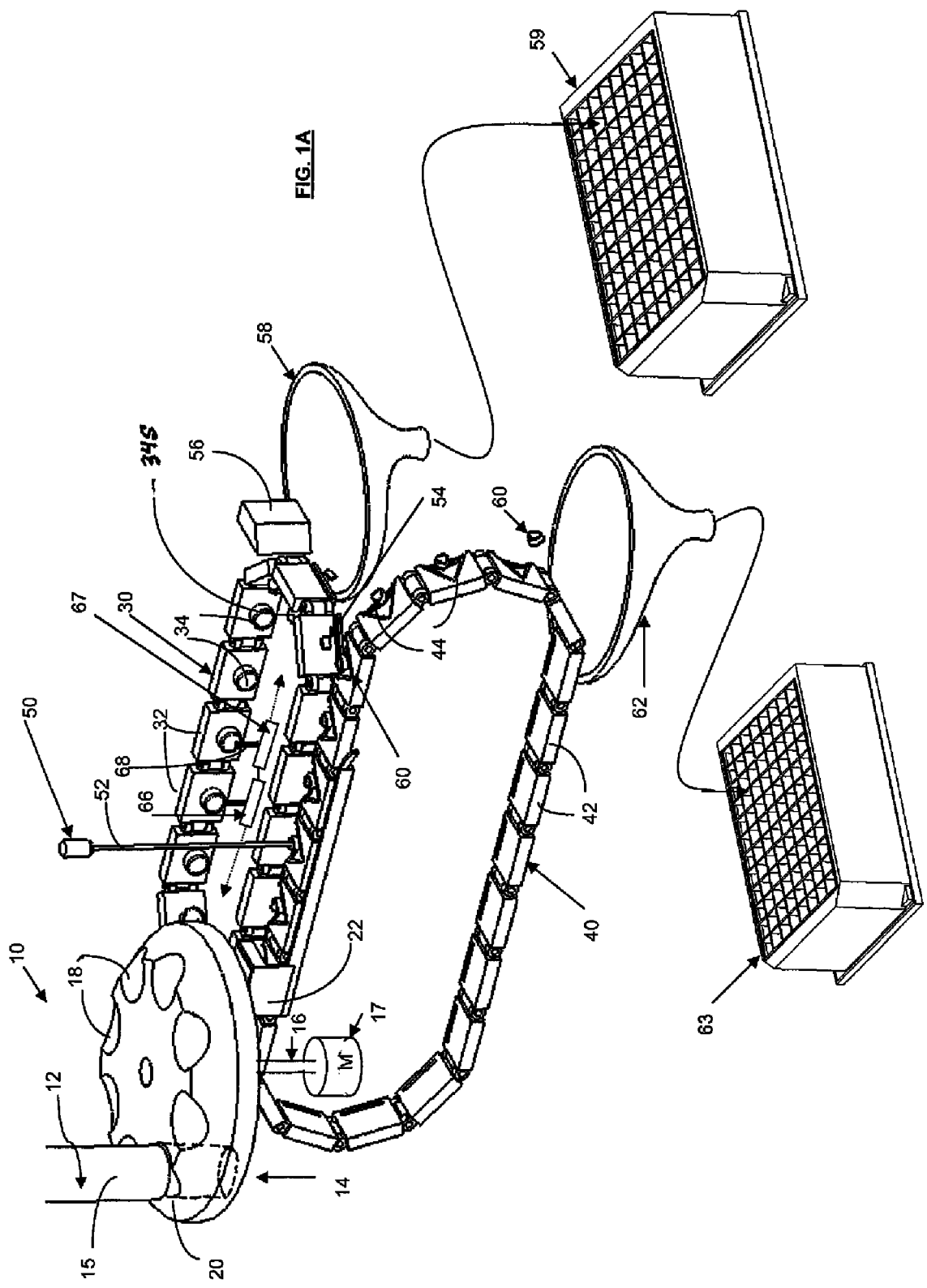
FIG. 1A is a perspective view of an exemplary embodiment according to one aspect of the present invention which magnetically orients a serial succession of individual seed relative to a laser beam to non-lethally sever and collect a sample from each seed.

FIG. 1A illustrates a system 10 that singulates seed that has been shelled from an ear of corn, orients each seed relative to a predetermined orientation, passes each seed serially under a laser beam to cut a sample clip from the seed, and delivers the cut seed and its corresponding sample clip into indexed containers.

Figure 1B:
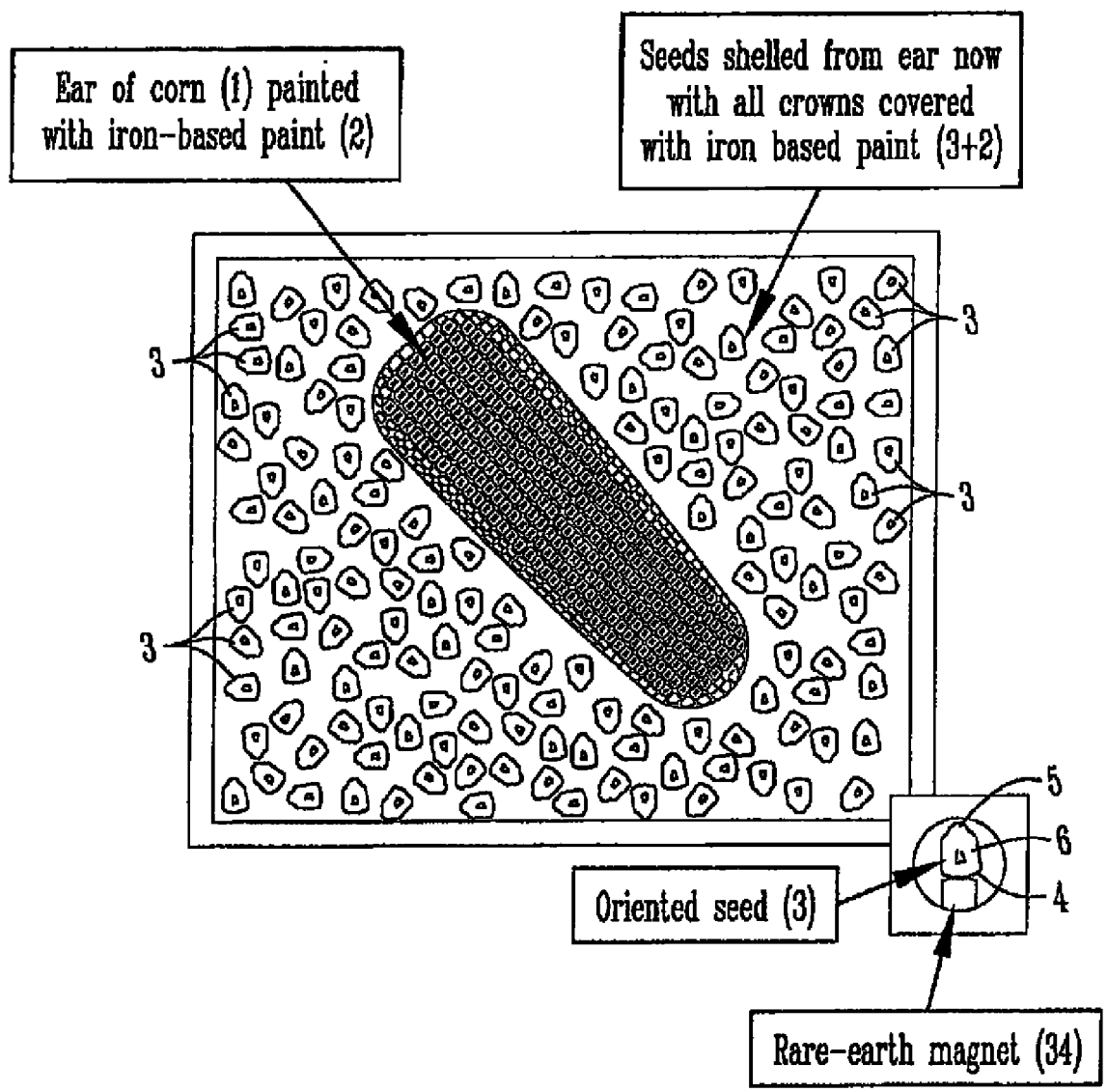
FIG. 1B illustrates an exemplary method of coating seed on an ear of corn with iron-based paint so that the crown of each seed will be attracted to a magnet once shelled from the ear.
Figure 1C:
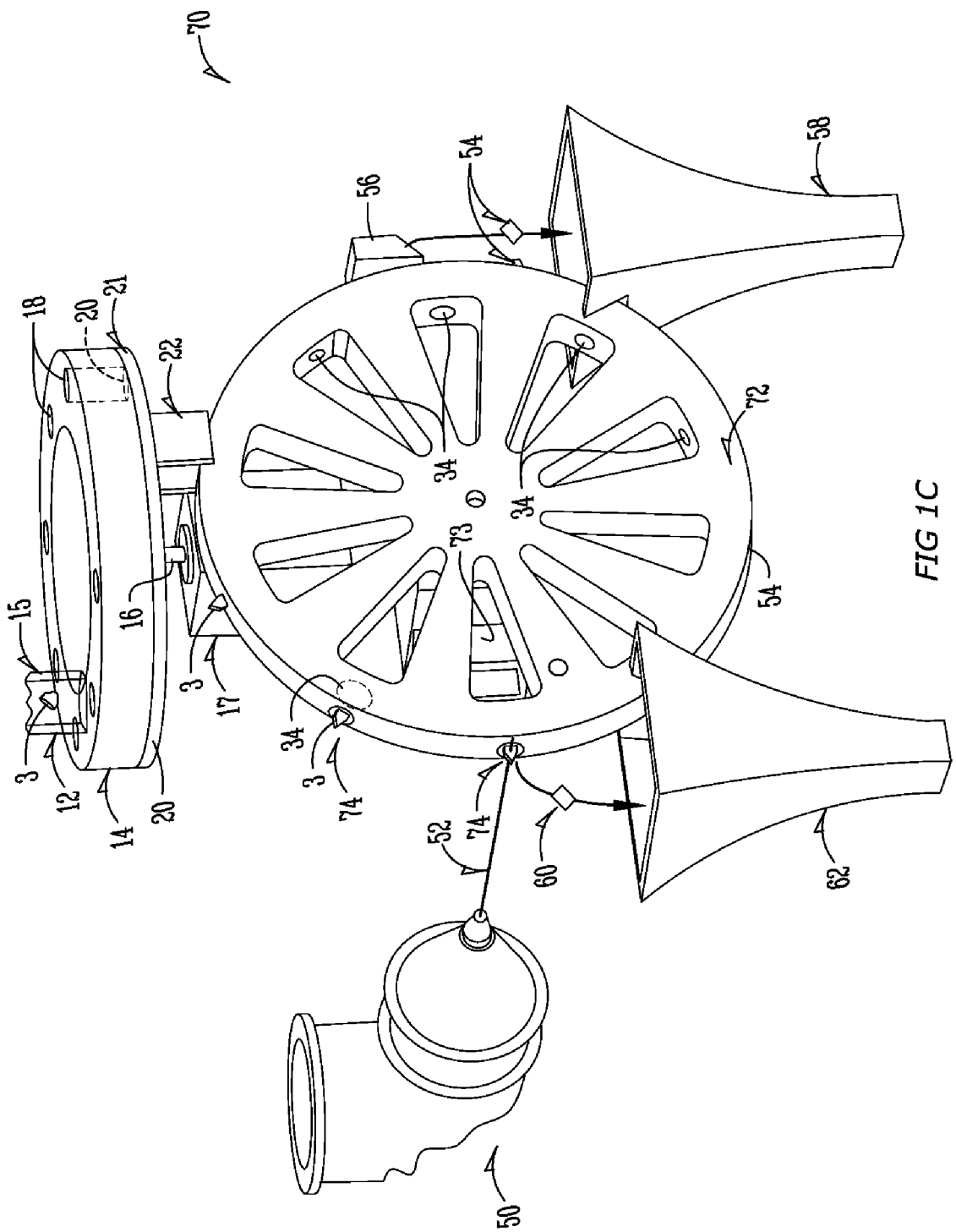
FIG. 1C is an alternative exemplary embodiment to that of FIG. 1A.

The embodiment of system 10 operates by pre-processing the corn kernels as illustrated in FIG. 1B. An iron-based paint 2 is applied (e.g. painted with brush or spray painted) on the exterior of an ear 1 of corn. The ear is then shelled to release the individual seed 3. Because the seed was painted on the ear 1 the iron-based paint 2 basically covers only the exterior or the crown portion of the individual seed 3.

Figure 1D:
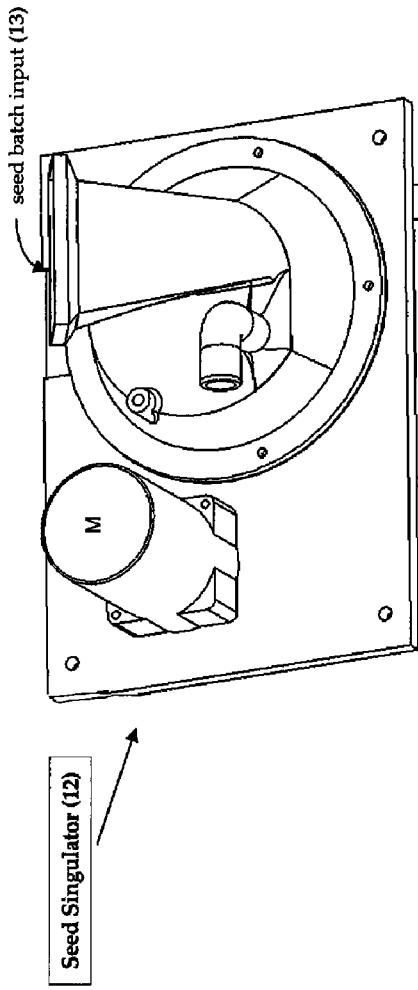
FIG. 1D is a perspective view of one example of a seed singulator that can be used with the systems of FIG. 1A or 1C.

The shelled painted seed is put into a seed singulator (an example is shown in isolation in FIG. 1D). Seed singulators are well known in the art and commercially available from a variety of sources. In this example, as illustrated in FIG. 1A, buffer wheel 14 rotates at a predetermined speed correlated to the speeds of conveyor 30 and conveyor 40. A motor 17 is connected to buffer wheel 14 by axle 16. Buffer wheel 14 has individual and equally spaced wells 18. Each well has an opening 20 at its bottom big enough for a seed to fall through. Wells 18 are dimensioned to capture one seed 3 at a time as individual seed are delivered from the seed singulator. The motors, wheels, conveyor 30, and conveyor 40 would operate in a complimentary fashion to buffer wheel 14 as follows.

A fixed, non-rotating plate (not shown but could be similar to plate 21 of FIG. 1C), would exist underneath buffer wheel 14 and have a single opening in correspondence with chute 22. Seed in each well or receiver 18 of buffer wheel 14 (which would rotate on top of the fixed, non-rotating plate) would thus be held in that position until the respective opening 20 of its well or receiver 18 comes into correspondence to chute 22. The seed in that well 18 in correspondence with chute 22 would fall through a hole 20 in bottom of well or receiver 18 and the hole in the fixed, non-rotating plate. Chute 22 would direct the seed into a V-shaped depression in a link 42 of conveyor belt 40. Each link 32 of conveyor belt 30 includes a magnet 34 on its back side. Conveyor belts 30 and 40 would both turn clockwise and concurrently in such a manner that a single link 32 would remain adjacent a corresponding single link 42. As can be appreciated, the timing would be set up to drop each seed 3 through chute 22 just ahead of its corresponding magnet 34 on a link 32 so seed 3 reaches the magnet 34 with precise timing.

In this manner, each seed 3 with iron-based paint that falls into a V-depression in a link 42 would be oriented such that the painted crown of seed 3 would be attracted and brought into abutment with link 32 because of the presence of magnet 34 on the other side of link 32. This would, conversely, orient the tip cap of each corn kernel 3 away from link 32.

As shown in FIG. 1A, each oriented seed 3 would proceed past laser 50. Laser 50 would be positioned and configured so that its laser beam 52 would sever a piece or clip 54 from each seed 3 (here it would slice off a sliver from the seed crown).

The V-depression in link 42 would retain the now separated cut seed 60 in position as it moves to the right in FIG. 1A. The clip 54 (which includes iron-based paint) would remain attracted and adhered to link 32 as conveyors 30 and 40 separate.

A scraper 56 could scrape or force each clip 54 from its corresponding link 32 and clip 54 would fall into sample collecting funnel 58. Instead of a scraper, a brush or brushes could be used to wipe clips 54 from belt 30. Alternatively, electromagnets could be used, and turned off to drop clips 54 into funnel 58. In another embodiment, the magnets 34 could momentarily separate from link 32 at a position directly above the sample collecting funnel 58 which would temporarily release the magnetic field and drop clips 54 (see reference numeral 34S, which is intended to diagrammatically illustrate the magnet 34 at that point being tilted away and down to release the sample 54). Optionally, a vacuum or forced air could be used to remove clips 54 from belt 30. A focused burst of air could be utilized in order to collect the clip from the wheel into a funnel or other such vessel.

As shown diagrammatically in dashed lines, sample collection funnel 58 would have a tube that would direct a first clip 54 into a designated well in sample well or plate 59. Each clip 54 would be directed to a separate well in well plate 59. The sample plate 59 could be moved so that the next well is under the tube as the next clip 54 drops, and so on, until all clips are in a respective well or the tray is full.

Correspondingly, each cut or sampled seed 60 would travel to the right on conveyor 40 until, by gravity, it would fall out of its link 42 into seed collection funnel 62. By appropriate components or procedures, each cut seed 60 would be directed to an individual well of well plate 63. It will be understood by one of skill in the art that a "well plate" means a multi-compartment device with multiple individual wells such as, but not limited to, a microtiter plate, a megatiter plate, a cluster plate, an index plate, a custom-designed plate containing multiple wells, etc., and in any "well plate," the number of wells can vary according to the requirement. Standard plates available in the industry include, but are not limited to, 6, 12, 24, 48, 96, 384, 864, 1536, and 3456 well plates. Some sampled seed may include residual, unintended magnetic paint. It is usually not enough for a magnet 34 to hold a sampled seed. A brush or wipe could be used to mechanically insure each sampled seed falls to the collection funnel.

As can be appreciated, corresponding clips 54 and cut seed 60 would be placed in analogous wells in well plates 59 and 63 so that laboratory results from clips 54 can be matched up with its corresponding seed at a later time (see, e.g., FIGS. 1E and 1F). The presence of magnetically active paint on the sample has not been found to significantly affect tests that might be performed on the sample in plant breeding, including, for example, genetic testing.

As can be appreciated, each conveyor 30 and 40 could be synchronized by appropriate gearing. FIG. 1A does illustrate that each magnet 34 could be held adjacent to a corresponding link 32 by a post 68 that extends from a link 67 of a conveyor belt 66 that is positioned underneath and is basically identical in size to conveyor belt 30. Each post 68 could be attached to its link 67 by a spring. Some type of object or mechanical part could deflect and tilt each post 68 away from belt 30 at position 34S to move the corresponding magnet away, as previously described, to cause clip 54 to drop. Once post 68 is past position 34S, it would spring back to position where its magnet 34 would be held against or closely adjacent to its link 32. Conveyor 66 could also be synchronized with belts 30 and 40 via appropriate gearing or other methods.

b) Operation (1) Pre-Processing (FIG. 1B)

As indicated in FIG. 1B, the iron-based paint covering the crown of each seed and magnets 34 are utilized to automatically position and orient each singulated seed relative to a laser beam. An example of such iron-based paint is available commercially, namely Krylon® Magnetic Spray Paint (product # 3151, 13 oz. aerosol spray can from The Sherwin-Williams Co., Krylon Products Group, Cleveland, Ohio USA). It can be sprayed onto the exterior of ear of corn 1 by conventional methods.

By empirical study, the amount of paint relative to the strength of the magnet can be established to create consistent positioning and orientation of seed. After the paint dries on ear 1, the ear is shelled by conventional means. One example is by an automatic sheller (e.g., Model SCS-2 Sheller from Agriculex Inc., Guelph, Ontario CANADA).

(2) Singulation

As can be appreciated, some sort of conventional singulator 12 (FIG. 1D is one example) could be positioned above a buffer wheel 14 for input of the shelled seed 3. Motor 17 (its shaft 16 would turn buffer wheel 14) could be connected to some type of digitally programmable controller or other similar device to control its speed and match it with the movement of conveyors 30 and 40. Alternatively, motors and transmissions could, by conventional adjustments, be configured and adjusted to operate in synchronization.

Singulator 12 singulates the seed from a bin of seed. There are a variety of commercially available seed singulators for such implements as corn or soybean planters that might be adapted and used. As indicated in FIG. 1D, singulator 12 includes an input 13 for receiving in batch or bulk form a plurality of seed. It outputs single seed from output 15 in a controlled manner.

Motor M turns buffer wheel 14 (not shown in FIG. 1D, but examples are shown in FIGS. 1A and C), which singulates individual seed in individual wells 18 or otherwise. Buffer wheel 14 delivers seed at a given interval consistent with conveyor belt 30. Buffer wheel 14 drops single seed 3 out of seed output 22 one at a time and is calibrated to be synchronized to drop a seed 3 on or very near each magnet 34 on wheel 72 (see FIG. 1C). Buffer wheel 14 is essentially a transitioning wheel between singulator 12 and conveyor 40.

(3) Orientation

Magnets 34 would attract the crown portion of each seed 3 because of the high magnetic activity of the iron in the iron-based paint. An example of magnet 34 is a neodymium rare-earth magnet. These tend to produce relatively strong magnetic fields for their size. Empirical testing can provide the correct magnetic strength of magnets 34 for a given iron-based paint and a given size and thickness of links 32 of conveyor 30.

The size of one example of magnet 34 is illustrated in FIGS. 1A-C (see particularly the isolated illustration in FIG. 1B, showing a magnet 34 and a single seed 3 of corn). It is preferable that the size of magnet 34 be as small as possible but provide sufficient magnetic field strength to attract and hold the iron-based paint located on the crown of a seed 3 in the position and orientation shown in FIGS. 1A-C, included as it moves in the systems of FIGS. 1A and 1C. The specifications for such a magnet might include, but are not limited to, a neodymium rare-earth magnet in a variety of shapes which range from 1/16" to 2" in length or diameter, from 1/16" to 1" in thickness, from 0.5 lbs. to 175 lbs holding force, and from a 11.5-14.5 Kilogauss surface field (e.g. rare-earth magnets from CMS Magnetics located at 1108 Summit Ave., Suite 8, Plano, Tex. 75074).

As previously described, in the embodiment of FIG. 1A, magnets 34 are fixedly mounted to posts 68 or other structure that hold against or in close proximity to and move synchronously magnets 34 relative to corresponding links 32 of conveyor belt 30, except at location 34S. Selection of the components is such that magnets will hold seed with magnetic paint or the clips with magnetic paint to the opposite side of the link until location 34S, where structure would move the magnet 34 at location 34S away enough that the magnetic attraction would attenuate enough that the clip 54 would drop by gravity from its link 32. Alternatively, magnets 34 might be attached by adhesive, interference fit, or other methods to the inside of each link 32 of conveyor belt 30 and be powerful enough to attract the iron-based paint through link 32, and use scraper 56 to remove clips 54, or some other method.

Magnetic conveyor belt 30 orients seed that have their crown covered with iron-based paint. Conveyor 40 is used for support.

The alternative embodiment of FIG. 1C mounts magnets 34 in through-holes in the rim of wheel 72 (e.g. by interference fit) such that a surface of each magnet 34 is directly exposed to the seed. Empirical testing can determine the precise desired magnet for a given embodiment.

(4) Sample Cutting

As indicated in FIG. 1A, laser beam 52 would cut off essentially just the crown of each seed 3. Because the seed 3 is consistently oriented, and because laser beam 52 can create a very clean and thin cut (a relatively small kerf of approximately 0.003" to 0.007"), system 10 allows severing of a clip 54 of sufficient quantity that it can be utilized for conventional laboratory analytical procedures to test for genetic constituents, seed components, etc., while leaving cut seed 60 intact and with a relatively high propensity to germinate. Thus, system 10 has been shown to be a non-lethal way to get sample tissue from corn seed without being substantially detrimental to the germination rate of the seed.

An example of a laser 50 that can be used is a sealed carbon dioxide ($CO_2$) laser. One example is a water-cooled Fire Star 201 Series $CO_2$ 200 watt laser, Model No. FSF201SB from Synrad, Inc. of Mukilteo, Wash. USA. A beam delivery system transfers the raw laser beam from the sealed laser and focuses it at the location the seed is to be cut. Such a beam delivery system can be purchased from Haas Laser Technologies Inc.; a 1.25 inch series beam delivery system with a 5 inch focal lens. Cut rate in this embodiment is 2 to 3 rpm and usually results in separation of the sample with one pass of the laser beam. The system could be set to allow two passes.

As can be appreciated by those skilled in the art, in this exemplary embodiment used for plant advancement experiments, it can be desirable that the amount of sample taken from the seed 3 have as little detrimental impact on germination potential as possible. This can also be desirable regarding the type of method of separating the sample from the seed. It can also be desirable that the amount of sample removed be enough (a useful amount) for meaningful results from any anticipated analytical procedures.

The location of the sample can be adjusted. In this example, the application of iron-based paint to the crowns and the geometry of the conveyors relative to the laser beam results in the removal of the crown as the sample, which contains endosperm. The laser can be adjusted to take an estimated amount of the seed crown from each seed. Because seed can vary in size (and tip cap to crown length), the actual sampled amount may vary from seed to seed, but the beam position can be adjusted by empirical testing and calibration of the laser. This allows a substantial amount of adjustability and accuracy in sample collection. The laser beam could be adjusted to instead remove the tip cap which can be an important structure for certain analysis. However removing the tip cap would likely prevent subsequent germination of the seed. Also, the iron-based paint could optionally be applied to other locations of the seed so that each seed would be oriented in other ways and, thus, samples could come from other areas of the seed, if desired. However, in this example, the goal is to sample the endosperm. It is preferable that the amount of sample be such that the ratio of pericarp to endosperm is as small as possible if using the sample for genetic analysis.

The size of clips or cut samples 54 can vary according to design. In the present example, the average size of clip 54 taken from maize seed was between 10 and 15 mg. For some purposes, an average size of about 20 mg was preferred. However, as stated above, a seed could be divided into almost any proportion of two parts, depending on the laser cut. There may be applications where about 60 mg of seed sample is desired, while other applications may require less than 60 mg, for example about 55 mg, 50 mg, 45 mg, 40 mg, 35 mg, 30 mg, 25 mg, 20 mg, 15 mg, or 10 mg may be desired. Some applications may require less than about 10 mg, for example, about 9 mg, 8 mg, 7 mg, 6 mg, 5 mg, 4 mg, 3 mg, 2 mg, 1 mg, 0.5 mg, or less than 0.5 mg may be desired. One of skill in the art will recognize that the size of sample taken from a given seed will vary based on the type of seed being sampled, the size of seed being sampled, and the intended analysis to be performed on the sample that is obtained.

Below are some examples of seed sample sizes for several different types of seed:

For Corn
Average mg weight per corn kernel is 260 mg (range is 150 to 350 mg)
Average desired sample size per corn kernel is 15 mg
For Soybeans
Average mg weight per soybean seed is 170 mg (range is 100 to 240 mg)
Average desired sample size per soybean seed is 10 mg
This correlates to 17% of the total seed weight for both crops. However, sample size can be whatever is desired. For example, seed sample size for some purposes may be much less than 17% of total seed weight. For some applications it could be on the order of 1%. For other applications it could be more than 17%. One example envisioned would be on the order of 20% of the seed weight. And, obviously, it could be other percentages either higher than 20% (e.g. about 20%, 30%, 40%, 50%, 60%, 70%, 80%, 90%, or about 100%, or any percentage or fraction of a percentage in-between) or lower than 1% (down to a fraction of 1% that is possible with the sampling method; or any in-between, including about 1%, 2%, 3%, 4%, 5%, 6%, 7%, 8%, 9%, 10%, 11%, 12%, 13%, 14%, 15%, 16%, 17%, 18%, 19%, and up to about 20%). However, it should be understood that depending on the species of seed, larger sample sizes may impact germination.

As can be appreciated, the sampling step can be further automated. For example, a sensor (e.g. proximity sensor) could be operably positioned to detect the presence of a seed at one or more locations along its intended path through the system. The sensor(s) can inform a controller or processor if a seed is at a location (or not). This information can be used to verify if a seed has or has not been at a location, which can be used to make assumptions as to whether a certain operation has or has not been performed on a seed. Other sensors, monitors, or controls can be used to synchronize, actuate, control, or otherwise assist the method and its automation. In the example of FIG. 1C, encoders on stepper motors could inform the system the exact position of wheel 72 (and each magnet on wheel 72) relative to a reference position or value.

(5) Collection of Samples

A variety of methodologies can be used to direct each clip 54 into a separate indexed well in index plate 59. There are commercially available machines that can accomplish the same. Alternatively, a delivery tube could be manually directed to successive wells.

Figure 1E:
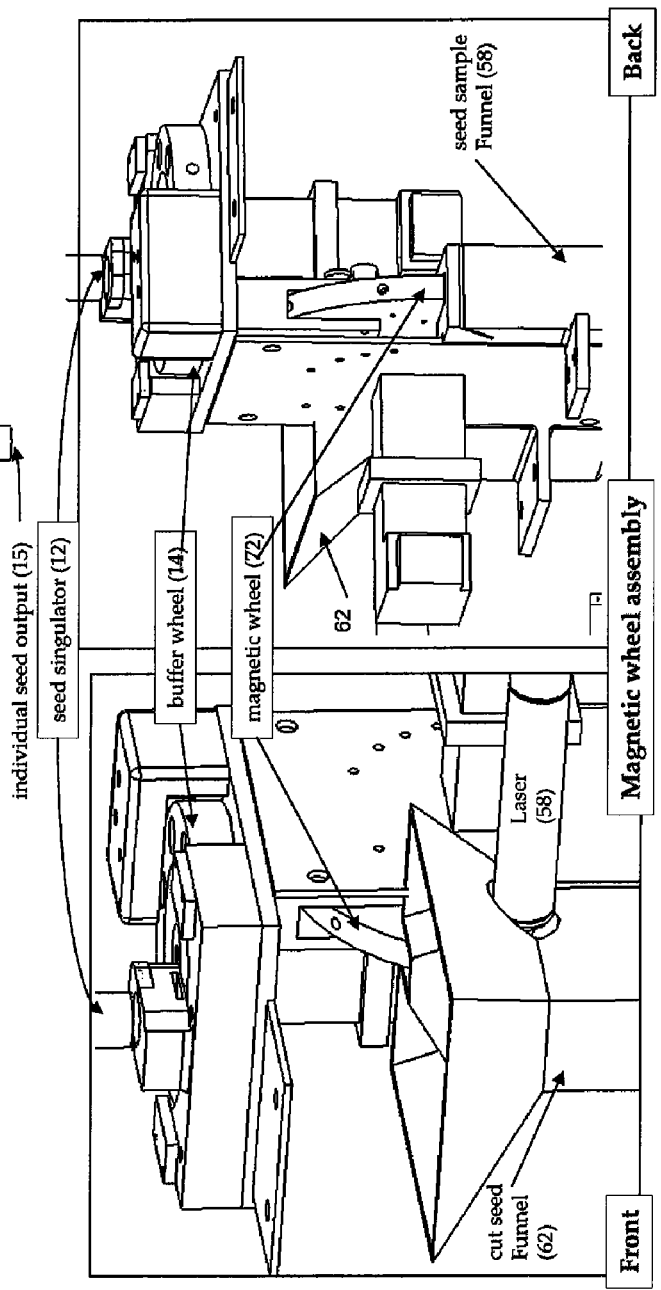
FIG. 1E is a perspective view of an example of a housing for supporting the components of the system of FIG. 1C.
Figure 1F:
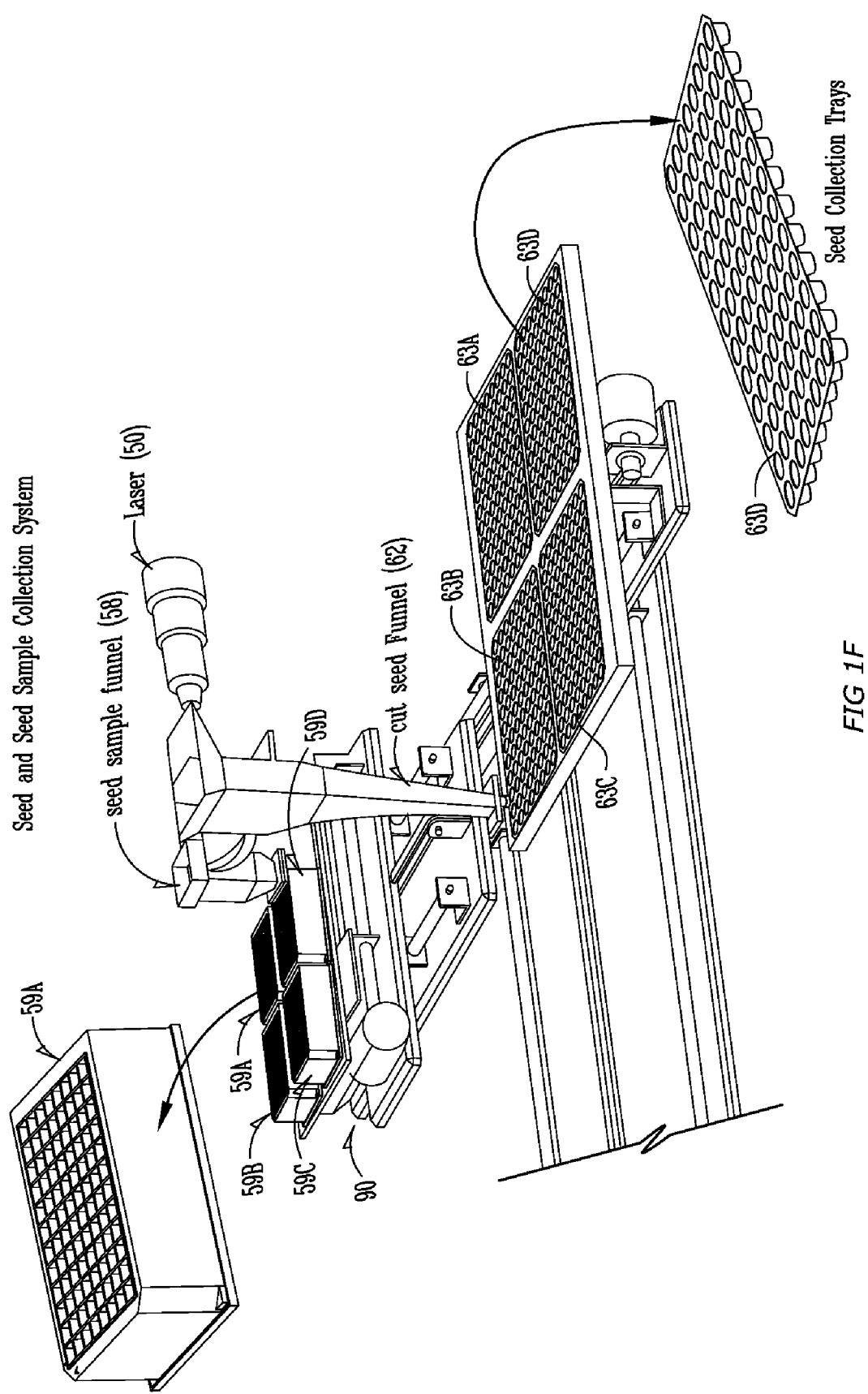
FIG. 1F is a perspective view of an example of sample and cut seed collection sub-systems for the system of FIG. 1C.

An example of an index plate 59 is shown in FIG. 1F, namely, a megatiter plate such as are well known (here having 96 individual wells).

FIGS. 1E and F show more details of an example of sample 54 and cut seed 60 collection.

As mentioned, a vacuum system could be added to use suction to help collect the samples and move them to a desired position.

(6) Collection of Cut Seed

Similarly, cut seed 60 (with clip 54 separated) could be directed to individual wells in well plate 63 and each cut seed 60 could be in the same or correlated well position in well plate 63 as its corresponding clip 54 in well plate 59.

An example of a well plate 63 is shown in FIG. 1F, namely, a seed collection tray such as are well known (here with 96 individual wells).

FIG. 1F illustrates that conventional commercially available XYZ positioners 90 and 95 can support four seed sample megatiter plates 59A-D and four corresponding seed collection trays 63A-D, and move them in synchronicity so that a first seed sample 54 would fall into x,y well 1,1 of plate 59A and a corresponding cut seed 60 would fall into x,y well 1,1 of collection tray 63A. Next sample 54 would fall into well 1,2 of plate 59A; and corresponding cut seed 60 (from which sample 54 was removed) would fall into well 1,2 of tray 63A). The process would continue in a like manner until either all samples are collected or all 96 wells of plate 59A and tray 63A are filled; at which time XYZ positioners 90 and 95 could move into position plate 59B and tray 63B and beginning filling wells 1,1 then 1,2 then 1,3 and so on, in a like manner.

(7) Timing

As can be appreciated, timing of buffer wheel 14 and movement of conveyor belts 30 and 40 (and conveyor belt 66, if used) can be coordinated by a variety of methods, including selection and adjustment of the corresponding motors or, in a more sophisticated system, using a digital programmable logic controller or other analogous means and methods.

(8) Post-Processing

Once clips 54 and cut seed 60 have been properly indexed in index trays 59 and 63, trays 59 and 63 can be taken to a location for further processing. In one example, clips 54 in indexing tray 59 would each be individually analyzed to obtain biochemical, genetic, or phenotypic information of interest. In one example, this process could be used as a part of a plant advancement experiment where genetic or phenotypic traits of interest are to be identified to decide whether corresponding cut seed 60 has commercially valuable or desirable genetic or phenotypic traits. If so, the cut seed can be identified for continued use in the plant advancement experiment. The cut seed 60 corresponding to the selected clip 54 can be easily and quickly identified by its corresponding index position in index tray 63 and can be shipped to an experimental growing location where it can be planted. As previously mentioned, system 10 is designed to have a substantially high probability that cut seed 60 will germinate at the growing location.

One type of biochemical analysis could include a protein assay which requires protein extraction from the clips or samples 54. One example of protein extraction is P-PER® Plant Protein Extraction Kit (Pierce Biotechnology). Other examples involve common grinding aids such as a mortar and pestle, Biomasher (Cartagen), or polypropylene pestle (Kontes) and a suitable extraction buffer. Other types of biochemical analysis could include oil or starch analysis. Still further types of biochemical analysis are possible and are well-known in the art.

One type of genetic analysis for the clips or samples 54 is DNA extraction. One example of DNA extraction is standard Extract N Amp (Sigma-Aldrich) protocol (other examples include, e.g., standard CTAB protocol and HotShot methods). Other types of genetic analysis, such as, but not limited to, RNA analysis, are also possible and are well-known in the art. Some analyses will include phenotype-based data in which specific seed morphologies are analyzed. A phenotype based analysis may be accomplished spectroscopically under a variety of light wavelengths. Alternatively it could be done manually by observation. In this scenario, the use of magnetically oriented seed allows the researcher to consistently hold an individual seed with specific reference to morphologies of interest. In this scenario the seed may be sampled or left unsampled so the spectroscopic or manual observations may occur. Specific observations may include, but would not be limited to, seed color, opacity, starch content, oil content and seed shape. As well known in the art, a variety of other observations are possible.

Bar codes could be used and created for each index tray 59 and 63 so that information about the contents of each can be recorded and stored and easily retrieved by scanning the bar codes. Commercially available equipment can be used for these functions and programmed to meet the needs of the application.

As can be appreciated, Embodiment 1 balances a variety of issues and factors to achieve at least the itemized objectives (a)-(f) discussed in the Background of the Invention.

(a) Viability

Controlled laser cutting of a sample has been shown to not significantly affect the germination potential for the sampled seed. By appropriate selection of power, beam width, intensity, type, speed of beam across the seed, and other controllable factors of laser beams, even relatively small seed can be sampled non-lethally. In the example of corn, the above-mentioned laser parameters allow a clip from the crown to be cut or severed non-lethally to the sampled seed. Laser cutting does not risk damage to the seed by crushing or tearing.

(b) Sample Amount

Controlled laser cutting can provide a useful amount of sample. As opposed to accumulating a volume of drillings, the laser can be adjusted to remove a monolithic piece of seed of sufficient size to obtain meaningful experimental results with conventional testing assays. The laser can be adjusted by relatively simple alignment changes to adjust the size of the sample.

(c) Sample Location

Not only size of sample, but sample location can be controlled. As mentioned previously regarding corn seed, sampling from certain seed locations may be undesirable (e.g. from at or near the germ because it can affect viability of the seed). The laser beam or the orientation of the seed can be adjusted accordingly. Automatic orientation can assist with this objective. Also, the relatively narrow laser beam assists in allowing substantial flexibility in sampling location, even for relatively small seed.

(d) Throughput

As shown in FIGS. 1A-F, a laser cutting and magnetic orientation arrangement lends itself to substantial automation. Seed can be feed in virtually a continuous manner serially through the laser beam. Orientation is automatic, as is sample and sampled seed collection. The level of automation can be selected by the designer. But even placement of samples and sampled seeds in containers or segregated locations can be automated. Thus, unlike the conventional methods of substantial manual, individual handling of each seed, these techniques, both individually and cumulatively, can greatly increase throughput relative to the amount of labor and time required.

(e) Avoiding Contamination

Controlled laser cutting and separating of sample from seed reduces risk of contamination of samples. The laser does not involve any hardware contact with the seed (as occurs with a drill or knife). The energy beam is transient and does not present risk of carry-over of residue or parts of one sample to another. And, as previously mentioned, the nature of and controllability of a laser beam allows substantial sample location accuracy, such that a sample from a given location is not contaminated with tissue from a different location of the same seed. Furthermore, as shown above, a laser lends itself to a method of sampling and handling each individual sample, ensuring no contamination between samples.

The laser beam is essentially a contact-free knife. The seed is severed much like it would be by mechanical cutting, however all of the material which is hit by the laser is ionized and there is no actual blade to risk any contamination on the next samples. The contact-free aspects also eliminate the risk of mechanical damage to the seed.

(f) Tracking Samples

As described with respect to this embodiment, substantial automation of handling of samples and sampled seeds can facilitate automated or semi-automated correlation between samples and the seed from which they were sampled, and/or between samples or between seed. This is valuable in efficient, quick, and accurate evaluation, selection, and further use of any samples or seed. Automated or automatic orientation and segregation and collection of samples and sampled seeds assist with this objective.

Note further that applying a magnetically active substance or component to the seed for automatic orientation assists in all of the above objectives, as well as assists in automation or at least semi-automation of steps to improve throughput of sample collection from plural seed. Laser cutting and automatic magnetic orientation assist in development of a semi- or fully automated system, from pre-processing to post-processing (and testing of samples); all of which promote high throughput for sample collection and use of samples. Feeding seed in bulk, automatically obtaining useful samples non-lethally, and automatically distributing samples and seed (while maintaining correlations) on a substantially continuous basis promotes high throughput.

This embodiment addresses the itemized objectives in the ways described above.

2. Embodiment 2

FIG. 1C

As can be appreciated, the basic idea of magnetic positioning, orientation and, laser cutting can be accomplished in a variety of different ways with a variety of different components and methodologies. FIG. 1C shows an alternative embodiment to that of FIG. 1A. A similar buffer wheel 14 with individual receivers 18 rotated by a motor 17 with shaft 16 is shown. Additionally, a stationary disc 21, having a single opening above chute 22, holds seed in each well 18 of rotating buffer wheel 14 except for the well directly over the opening in disc 21 in alignment with chute 22. In this manner, individual seed 3 is dropped, one at a time and at spaced apart intervals.

In FIG. 1C, a vertically positioned wheel 72 has magnets 34 at spaced apart positions as shown. As wheel 72 turns by chute 22, singulated seed are deposited in correspondence with the location of each magnet 34. Seed 3 have crowns painted with iron-based paint. Each seed 3 would thus be both automatically positioned and oriented so that its crown is in abutment with the corresponding magnet 34. Thus, the tip cap is extended outwardly.

The receiver locations 74 along wheel 72 (corresponding with locations of magnets 34) would rotate past laser beam 52 of laser 50. Cut or sampled seed 60 would serially drop by gravity into seed collection funnel 62. Seed clips 54 from the sampled seed would follow around and be serially knocked off the exterior of wheel 72 by scraper 56 and fall into sample collection funnel 58.

In a similar manner to that of the system of FIG. 1A, this singulates seed, presents them in a consistent position and orientation relative to a laser beam, and allows a relatively precise ability to cut off a portion of each seed, collect clips 54 for use in procedures such as biochemical, genetic, or phenotypic analysis, and collect the cut seed for possible planting.

Similar to Embodiment 1, Embodiment 2 likewise balances issues and factors to achieve some measure or level of all the itemized objections (a)-(f) from the Background of the Invention. The highly controllable, location-specific sample taking with laser cutting which has been shown to not significantly affect the germination potential for the sampled seed and provide a useful amount of sample. Automatic orientation can be used, including magnetic orientation. Risk of contamination of samples is controlled. It can be highly automated for high throughput for sample collection and use of samples, as well as effectively track samples.

3. Options and Alternatives

As can be appreciated, magnetic orientation and/or laser cutting can take various forms and embodiments. Variations obvious to those skilled in the art will be included within this description. The timing of the components can be coordinated by empirical testing. The amount of sample from each seed can be adjusted by adjustment of the laser beam.

Substances that can be magnetically attracted by magnets could be applied in different ways to the seed. A possible example is to basically powder coat a portion of the seed with a mixture that includes high magnetic activity material that would be attracted to a magnet. Another such example is to use a fine spray glue to coat seed, or if the plant structure on which the seed are found is appropriate, such structures (i.e. corn cobs) could be dipped into a glue "bath" allowing the outer surfaces of the seed to be coated with glue. The seed with wet glue on them can then be brought into contact with particles, such as ferrous, magnetite or hematite particles, which would be attracted to magnets. Additionally, electrostatic substances could be used to charge the surfaces of seed in order to have better adherence of the substances to the seed. One of skill in the art will recognize that various such methods could be used to obtain the desired result of having the seed partially coated or fully coated with an electrostatic substance.

It may not be necessary to remove the iron-based paint from the sample 54 or cut seed 60. However, it could be done. It could be physically removed (e.g. by abrasion) or chemically removed. A number of paint removing methods are well known. The method selected would be based on the intended use of the sample 54 or cut seed 60.

Additionally, electromagnets might be used instead of permanent magnets. The magnetic field could be turned on to hold, position, and orient the seed for cutting by the laser beam, but then turned off to drop the magnetically attracted part by gravity. Such electromagnets and associated components are commercially available from sources like AEC Magnetics, 10200 Springfield Pike, Cincinnati, Ohio USA 45215.

Similar seed collection and sample collection to that of FIGS. 1A-1F could be used, or other methods are possible.

C. Second Concept

Magnetic Orientation and Simultaneous Chopping of Samples from Plural Seed (FIGS. 2A-C)

1. Embodiment 1 a) Apparatus (FIGS. 2A and 2C)

Magnetic orientation is also used in system 100 of FIG. 2A. Magnet assembly 102 includes a base plate and a plurality (in this example forty-eight) posts 104 extending downwardly from the base plate. A magnet 106 is positioned at or near the distal end of each post 104.

Posts 104 of magnet assembly 102 are inserted into complementary through-holes 112 in cutting assembly 110. The cutting assembly box or housing slideably retains cutting blade 114 in slot 116. Cutting blade has forty-eight openings 115 corresponding in position and spacing to the forty-eight through-holes 112, but the perimeter of each opening 115 is formed, sharpened, or otherwise configured to include a relatively sharp edge.

The combination of the magnet assembly 102 and the cutting assembly 110 is simultaneously lowered into seed box 108 (see FIG. 2C) filled with a mass of singulated seed 3, each with its crown painted with iron-based paint, as previously described. Each magnet 106 would ideally pick up and automatically position and orient a seed 3 so that its crown is in abutment with magnet 106 and its tip cap extends outwardly and distally.

Base 123 includes on its upper side foam pad 122 to secure seed for cutting. There could be small rings or other similar retainers in correspondence with through-holes 112 when the cutting assembly 110 is positioned on top of base 123 and are used to secure seed for cutting.

b) Operation

(1) Pre-Processing (FIG. 1B)

Ear corn 1 is pre-coated with iron-based paint. After the paint is dry, ear 1 is shelled and put into a bin (see FIG. 1B).

(2) Singulation

The combination of the magnet assembly 102 and the cutting assembly 110 is simultaneously lowered into the bin of seed 3 (each with its crown covered by iron-based paint) to singulate seed 3, one to each post 104 by the attraction of the iron-based paint to a magnet 106 in each post 104.

(3) Orientation

Each seed 3 is automatically oriented crown-to-magnet because of the iron-based paint on the crown of seed 3. The tip cap of each seed 3 extends distally.

Figure 2E:
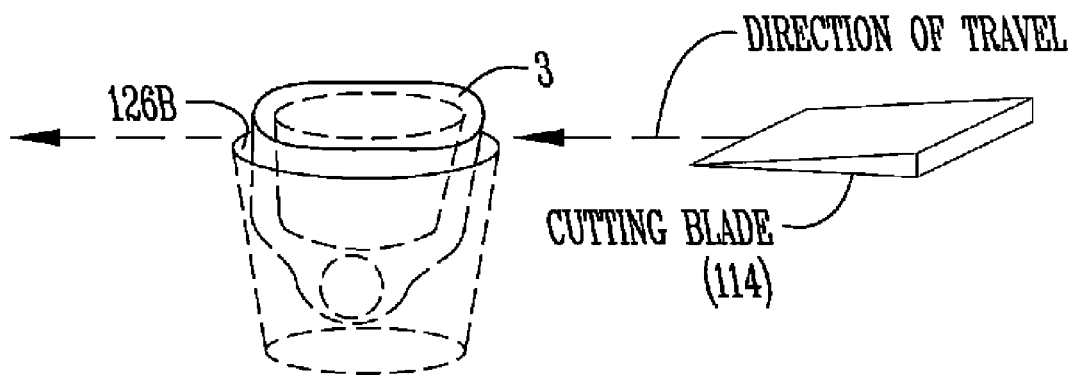

FIGS. 2D and E illustrate an optional and alternative method of positioning, holding, and orienting seed prior to sampling. Instead of a funnel through which the seed can freely pass or a cylindrical cavity to retain a seed, a tapered conical well or receiver 126B can be formed in base 123 (see FIG. 2B) for each of the twenty-four positions. The cavity that defines the well would be designed like an inverted truncated cone (see conical well 126B in FIG. 2D). Well 126B would be formed in a solid plate or with a side wall of that shape. As indicated in FIG. 2E, the dimensions of well 126B would be designed so that for conventional sizes of corn kernels, the tip cap end would fit first, but the opposite end with the crown would extend above the plant of well 126B. This takes advantage of the natural shape of corn kernels to not only position and orient the kernel crown-up, but also to leave a portion exposed and outside well 126B. A blade 114 would then be configured to move across a plane (indicated by arrow in FIG. 2E) to cut off crown samples from the part of each seed exposed above its well 126B. As can be appreciated, each seed could be dropped tip-cap-down into its well 126B. However, for corn and its shape, the geometry of well 126B would tend to promote the tip-down orientation, even if not exactly pre-positioned in that way. Once in well 126B, the geometry of well 126B influences the position and orientation of seed 3. In this example it helps hold and maintain an orientation where the endosperm can be samples.

(4) Sample Cutting

Magnet assembly 102 and cutting assembly 110 are placed on top of base 123 so that through-holes 112 are in correspondence with rings 125 on foam pad 122 of base 123. Blade 114 is located in a position such that its openings 115 are in correspondence with through-holes 112. The magnet assembly 102 and the cutting assembly 110 position the oriented seed 3 such that the tip cap is in abutment with, and slightly compressed against, foam pad 122, but the plane of the cutting edges of openings 115 of blade 114 are aligned just below the crowns of seed 3.

A clamp (e.g. see FIGS. 2B and 2C for examples) secures the combination of base 123, cutting assembly 110, and magnet assembly 102 together. Seed 3 would therefore be oriented by magnets 106, and the structure of the combination would hold seed 3 in that position.

Blade 114 would then be slid in the appropriate direction in slot 116 to move cutting edges of openings 115 into and through each seed 3 to sever a portion of the crown of each seed 3. One example of operation of cutting by blade 114 is shown at FIG. 2C. The combination could be turned on its side, as shown. An arbor press could be operatively connected to handle 118 of blade 114 and operated to push or pull blade 114 to cut seed 3.

(5) Collection of Cut Seed

After cutting with blade 114 the magnet assembly 102 and cutting assembly 110 are inverted, the clamps are released, and the base 123 is removed (e.g. see FIG. 2A). The cut seed 60 are located in the wells of the blade 114 and are separated from the seed clips or samples 34 as a result of the blade 114 moving sideways during the cutting procedure. The magnet assembly 102 and cutting assembly 110 can then be inverted again over a 48-well tray to collect and index the cut seed 60.

(6) Collection of Samples

Withdrawal of the magnet assembly 102 from cutting assembly 110 releases the magnetic attraction imposed on the seed clips or samples 34. In this embodiment, the seeds with the magnetically active paint on them are never directly bound to the magnets of the magnet assembly 102. At the bottom of each well in the cutting assembly 110 there is a thin $1/16"$ layer of plastic upon which the magnets rest. The layer is thin enough that the magnetism still permeates through the plastic and attracts the iron-based paint covered seed. When the magnet assembly 102 is lifted the seed chips are released because the plastic prevents them from going with the magnet assembly. In addition the movement of blade 114 back to its original position exposes the seed clips or samples 34. The samples 34 are deposited into a corresponding well of a forty eight well index tray.

(7) Post-Processing

Similar to what has been previously discussed, the seed clips or samples 34 can be processed by known-in-the-art processes to derive biochemical, genetic, or phenotypic information about seed 3. The biochemical, genetic, or phenotypic information can be used by plant scientists to select which seed is to be further used in a plant advancement experiment or other plant-based research and development. The cut seed 60 that corresponds with the selected seed clip 34 (by virtue of matching its position in the cut seed index tray with the position of the selected clip or sample in the sample index tray), can then be transported or shipped to the appropriate growing location and planted and grown for further use in the experiment.

Embodiment 1 of the second concept also balances a variety of issues and factors relative to the itemized objectives (a)-(f) of the Background of the Invention.

(a) Viability

Cutting or chopping with reasonably sharp blade edge(s) through a seed to sever a sample can be controlled to not significantly affect the germination potential for the sampled seed. By appropriate selection of blade edge, material, force, speed, range of movement, and other controllable factors of blades, even relatively small seed can be sampled non-lethally. In the example of corn, the blade and cutting parameters allow a clip from the crown to be cut or severed non-lethally to the sampled seed.

(b) Sample Amount

Automatic orientation with magnetics assists throughput as well as obtaining useful samples. Controlled cutting with a blade can provide a useful amount of sample. As opposed to accumulating a volume of drillings, the blade can be adjusted to remove a monolithic piece of seed of sufficient size to obtain meaningful experimental results with conventional testing assays. The blade can also be adjusted by relatively simple alignment changes to adjust the size of the sample.

(c) Sample Location

Not only size of sample, but sample location can be controlled. As mentioned previously regarding corn seed, sampling from certain seed locations may be undesirable (e.g. from at or near the germ because it can affect viability of the seed). The orientation of the seed can be adjusted accordingly. Automatic orientation can assist with this objective.

(d) Throughput

This second concept can be automated or configured, at least in part, to increase efficiency and throughput over handling individual seed one-by-one from sample taking to further use. Simultaneous cutting by chopping blade a plurality of seed promotes high throughput. As shown in FIGS. 2A-C, the apparatus can be designed to concurrently slice or cut a sample from a substantial number of seed (e.g. 24 or 48 or more). Although in these examples some manual handling is required (e.g. to place the magnet assembly 102 and cutting assembly 110 into a batch of seed having crowns coated with magnetically active paint and then placing the magnet assembly 102 and cutting assembly 110 into the base 123), once the plural seed are each grabbed and automatically oriented by plural magnets, sample collection for that set of seed is relatively rapid because all samples are taken essentially simultaneously. Over time, and many sets of seed, this can improve throughput. Magnetic orientation arrangement lends itself to substantial automation. Orientation is automatic. As described above, sample and sampled seed collection is quite efficient and quick. For example, even placement of samples directly into a well plate of at least a corresponding number of wells as magnets, can provide a level of throughput that is significantly better than conventional seed sampling methods.

(e) Avoiding Contamination

Cleanly chopping a sample from the sampled seed and keeping it segregated controls risk of contamination of samples. For example, cutting by blade does not normally produce debris, particles, or dust that could cause contamination issues. A monolithic sample clip from the seed is created. Even though, unlike a laser beam, the blade would physically abut the seed, dust and debris is generally not created. Cleaning of the cutting edges may be desirable after each cut, but may not be needed.

(f) Tracking Samples

Substantial automation of handling of samples and sampled seeds can facilitate automated or semi-automated correlation between samples and the seed from which they were sampled, and/or between samples or between seed. Automated or automatic orientation and segregation and collection of samples and sampled seeds assist with this objective.

Note further that applying a magnetically active substance or component to the seed for automatic orientation assists in all of the above objectives, as well as assists in automation or at least semi-automation of steps to improve throughput of sample collection from plural seed.

This embodiment represents a less complex, lower cost, and more portable system than laser cutting. It also achieves a level of high throughput, although it involves batch processing of sets of seed and some manual handling.

2. Embodiment 2

FIG. 2B

FIG. 2B illustrates a similar embodiment to that of FIG. 2A with the following notable differences.

The magnet assembly has twenty-four magnetic posts instead of forty-eight.

Instead of a foam pad to help hold seed 3 while cutting with blade 114, spring-loaded posts 128 are used. Posts 128 are mounted to a plate 130 that can be inserted into and removed from base 124 through slot 132. The twenty-four spring-loaded posts 128 are biased outwardly by springs, but can be depressed with sufficient force against their distal cup-shaped or funnel-shaped ends.

The cut seed 60 would be collected similarly to that described in the previous embodiment.

Note that FIG. 2B shows an optional 24-well funnel 140, with twenty-four wells 142 on top, each of which terminates in a bullet tube 144 at their bottom. When the combination of FIG. 2B is unclamped and separated after cutting and collection of cut seed 60, funnel 140 can be positioned over one quadrant of a conventional ninety-six well sample plate. Seed clippings 34 are released from the magnet assembly as described in the previous embodiment, directed into the funnel 140, and collected into separate wells of one quadrant of the ninety-six well sample plate.

The second embodiment of the second concept balances issues and factors on seed sampling in similar ways to the first embodiment of this second concept. It addresses the itemized objectives (a)-(f) in similar ways.

3. Options and Alternatives

Variations obvious to those skilled in the art will be included within this description. The size and configuration of components can be selected according to need and desire.

Note that FIG. 2C illustrates an optional sample collection method. A set of bullet tubes can be held in corresponding locations to the twenty-four positions of the funnel 140. The seed clippings 34 are first collected in a bullet tube instead of collecting them directly into a standard ninety-six well sample plate. The twenty-four bullet tubes can be inverted and moved into one quadrant of the ninety-six well sample plate (see pictures "e." and "f." of FIG. 2C.) The cutting process could be repeated three more times to fill the other three quadrants of the ninety-six well sample plate. Once full, biochemical, genetic, or phenotypic testing could proceed for ninety-six samples. The cut seed 60 corresponding to each of the ninety-six samples could be collected and indexed with another ninety-six well plate, or with four twenty-four well plates, as shown in picture "d." of FIG. 2C.

As indicated above the sample plate is configured with ninety six wells, which is a conventional number for many analytical methods practiced by plant scientists. Other sizes of sample plates are also a possibility, such as 12, 24, 48 and 384 well models.

D. Third Concept

Sequentially Drill Individual Seed and Collect Debris by Vacuum (FIGS. 3A-F)

1. Embodiment 1 a) Apparatus (FIGS. 3A-3D)

FIG. 3A shows a singulated seed 3 that has been shelled from an ear of corn. Unlike the embodiments of the first and second concepts (discussed above), seed 3 is not painted with iron-based paint. It is oriented on a surface relative to a drill bit 203 (e.g. 0.035 inch dia.) of a hand-held drill 202 (e.g. any of a number of rotary tools from Dremel of Racine, Wis. USA, e.g. Model #395 type 5) operated at, for example, approximately twenty-thousand rpm. It is understood by one of skill in the art that a wide range of rpms is encompassed. For example, rpms ranging from 50 rpm through to several hundred thousand rpm would be encompassed by this embodiment.

Drill 202 is modified to include a transparent (e.g. plastic) cone 206 around bit 203. Cone 206, along with the length of bit 203, functions as a de facto depth gauge for drill 202. The geometry of the interior of cone 206 would act as an end limit for depth of drilling of bit 203 (e.g. micro carbide) relative to kernel 3. Drill 202 also accepts a range of diameters of bits 203 in its chuck.

Drill 202 is also modified to put a vacuum or aspiration source in fluid communication with the interior of cone 206 by vacuum tube 208. When the vacuum source is applied to vacuum tube 208 and drill 202 is operated to drill into seed 3, debris separated from seed 3 by the drilling is aspirated through vacuum line 208 to a distal end of vacuum line 208.

FIGS. 3B-D shows a vacuum box 212 to which a vacuum pump 213 is operatively connected in fluid communication. Operation of vacuum pump 213 (e.g. a conventional, commercially available 5½ hp, 16 gallon shop vacuum with 1¼ inch i.d., 2¼ inch o.d. hose) evacuates air from vacuum box 212. A multiple well sample plate 214 with bottom openings to each well is mounted over an opening in the top of vacuum box 212. An air-permeable filter 216 is placed between the bottom of the vacuum box 212 and vacuum box 212. As shown at FIG. 3D, distal end 209 of vacuum line 208 is simply placed in fluid communication with the appropriate well of sample plate 214 corresponding to the seed 3 being drilled, and the debris is vacuumed, transported, and deposited in that well by the suction generated by the partial vacuum in vacuum box 212. When a desired amount of debris from seed 3 is deposited in that well, drilling is discontinued, seed 3 is indexed to the depositing debris, the distal end of vacuum tube 208 is placed into the succeeding well in sample plate 214, and the next seed 3 is drilled and its debris deposited in sample plate 214.

As indicated in FIGS. 3B and C, sample plate 214 is configured with ninety six wells, which is a conventional number for many analytical methods practiced by plant scientists. Other sizes of sample plates are also contemplated, such as 24, 48 and 384 well models.

FIGS. 3A and B show an optional feature of modified drill 202. A pressurized air source (not shown but could be, e.g., a home shop or garage size air compressor) could be connected in fluid communication with cone 206 (here from an opposite side to vacuum tube 208) by pressurized air tube 210. At selected times (e.g. after the drilling of each seed 3), the distal end 209 of vacuum tube 208 could be removed from sample plate 214 and the pressurized air source turned on to clean out vacuum line 208, cone 206 and bit 203.

b) Operation

(1) Pre-Processing (FIG. 1B)

The only pre-processing of seed 3 is that it be shelled from its ear and singulated so that it can be manually placed in position for drilling.

(2) Singulation

As can be appreciated, the worker will usually keep track of the origin of the singulated seed 3 so that correspondence between each seed, its origin, and the debris from its drilling can be maintained.

(3) Orientation

The worker would manually manipulate seed 3 and drill 202 to select the location for drilling of seed 3.

(4) Sample Drilling

The size and depth of bit 203 would be pre-selected to correspond with the amount of debris to be collected from seed 3.

As discussed previously, it is preferably that the amount of debris, depth of drilling, and other handling of seed 3 generate sufficient debris for accurate biochemical, genetic, or phenotypic testing of the debris and with minimal effect on germination potential of seed 3 after the drilling.

It has been found to be advantageous to use a spongy, clay-like, or sticky surface on which to drill the seed to hold it in place during drilling and also enhance the vacuuming up of debris from the drilling.

(5) Collection of Samples

In the present example, the average size of debris was between 0.5 and 20 mg.

(6) Collection of Cut Seed

Drilled seed 60 could be directed to individual wells in an appropriate well plate in the same or correlated well position as its corresponding debris in sample plate 214.

(7) Timing

The amount of drilling time can be adjusted as needed or desired, but preferably would be minimized so long as sufficient amount of debris is obtained.

(8) Post-Processing

Biochemical, genetic, or phenotypic testing of debris can proceed as previously described. Drilled seed correlated to debris that contains desired biochemical, genetic, or phenotypic traits can them be used accordingly.

Embodiment 1 of this third concept also balances the variety of issues and factors relative to itemized objectives (a)-(f) of the Background of the Invention.

(a) Viability

Controlled drilling of a sample has been shown to not significantly affect the germination potential for the sampled seed and provide a useful amount of sample. By appropriate selection of drill bit size, configuration, and material, and drilling force, speed, range of movement, and other controllable factors of drills, even relatively small seed can be sampled non-lethally. In the example of corn, the above-mentioned drill and drilling parameters allow drillings from the endosperm to be removed non-lethally from the sampled seed.

(b) Sample Amount

Sample amount can be controlled in quantity by control of bit size and speed, and depth of drilling, to control amount of seed debris or sample separated from the seed. Sampling can be controlled to reduce risk of removal of too much sample.

(c) Sample Location

Not only size of sample, but sample location can be controlled. As mentioned previously regarding corn seed, sampling from certain seed locations may be undesirable (e.g. from at or near the germ because it can affect viability of the seed). Drilling can be controlled manually or otherwise. The orientation of the drill bit to the seed can be adjusted accordingly. Manual control of the drill and some operator training and skill facilitate this. Orientation could assist with this objective. For example, as described with respect to FIGS. 2D and E, a multi-well tray or plate could be configured to have a receiver for each seed that facilitates orientation of the seed. Plural seed could be placed in position in such receivers. The drill could then be moved from seed to seed for individual sampling of each seed. The consistent orientation (e.g. crown-up for corn seed) would expose an appropriate position for sample taking.

(d) Throughput

Although drilling, in one embodiment, is done manually, automation or at least semi-automation of some of the steps improve throughput of sample collection. Other procedures could assist throughput. For example, placement of plural seeds in wells or receivers in preparation for sequential drilling and sample collection is another way to increase throughput. A set of seed would be at least laid out and partially oriented and supported in preparation for drilling. Additionally, handling of samples by automatically pulling drillings down to separated locations on a filter by vacuum can be quicker than collecting debris from each seed and then manually transferring each sample quantity to a container or well.

(e) Avoiding Contamination

Vacuum collection of the sample reduces risk of contamination of samples. Use of pressurized air to clean the drill and tubing reduces contamination risks and improves throughput. Even though drilling can create or disrupt some dust or debris, and the bit would physically abut the seed, and successive seed, vacuum collection around the seed reduces risk of contamination. Cleaning of the bit may be desirable after each sample, but may not be needed or may reduce contamination risk over sample collection methods that do produce or disrupt dust or debris. Automatic or semi-automatic cleaning of the bit by use of pressurized air is one cleaning technique to reduce risk of cross-contamination. Cleaning between samples can be with forced air and/or vacuum, or drilling into an inert material prior to hitting the next sample.

Using vacuum, anything above the well or the seed being drilled is accumulated to a single point. In some of these embodiments, the sample debris is accumulated to a single point or area on a filter paper or sheet in a plate. Adding the filter further reduces risk of contamination by fine particles that might escape the vacuum source. Also, vacuum allows collection of the sample without modification of the sample.

(f) Tracking Samples

Substantial automation of handling of samples and sampled seeds can facilitate automated or semi-automated correlation between samples and the seed from which they were sampled, and/or between samples or between seed. Automated or automatic orientation and segregation and collection of samples and sampled seeds assist with this objective.

With respect to the drilling embodiment, a balancing of the itemized objectives occurs. While the described embodiments do involve some manual actions and, thus, throughput may not necessarily be as high as some other embodiments, the apparatus and methods are not highly complex or costly, can be efficiently taught, and are relatively economical.

2. Embodiment 2

FIGS. 3E-F

Figure 3F:
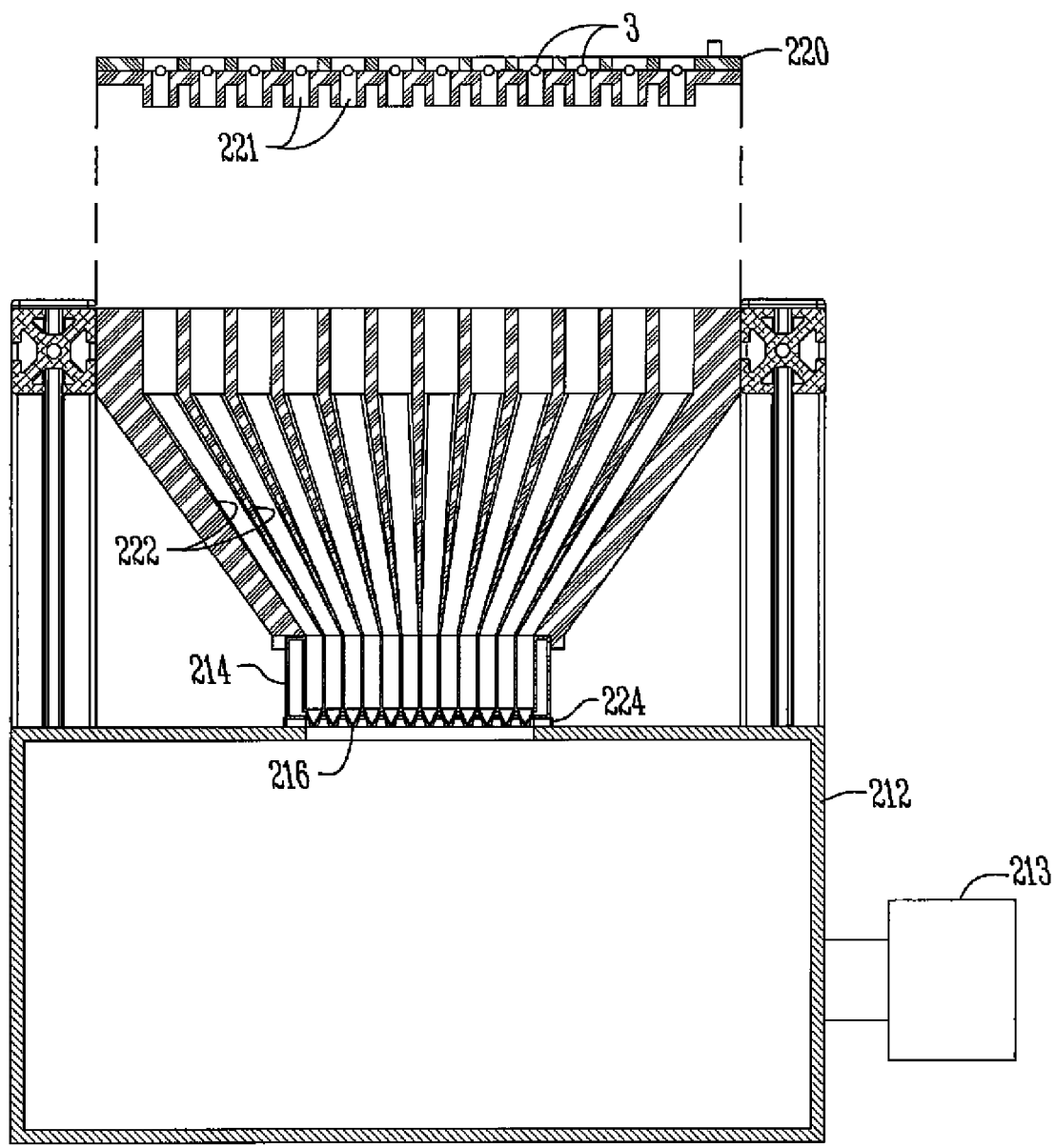

A variation on the concept of FIGS. 3A-D is illustrated in FIGS. 3E-F. A seed tray 220 with ninety-six seed wells is mounted by a frame above the sample tray 214. Ninety six tubes 213 are connected to a manifold with individual openings 221 that correspond to complementary openings in the seed tray 220 and each well of sample tray 214. FIG. 3E shows just one tube 213 for clarity of illustration; FIG. 3F shows all ninety six tubes.

Ninety six seed 3 are placed, one to a well, in the ninety six wells of seed tray 220. Vacuum source 213 is turned on which pulls a vacuum in vacuum box 212, as previously described. Drill bit 203 of drill 202 is then inserted by the worker manually into the first well of seed tray 220 and the seed 3 therein is drilled an appropriate amount. Debris from the drilling is thus automatically pulled out the manifold bottom 221 of the well, through corresponding tube 213, and into the corresponding well in sample tray 214. The filter 216 under that sample tray well allows suction through tube 213 to bring the debris to the sample tray well, but stops and collects the debris in that sample plate well.

This embodiment generally positions each seed 3 for immediate sample collection, at least in a localized seed tray well. The openings to the wells of the seed tray 220 are big enough to allow entry to bit 203 and perhaps part of the chuck. They could have a truncated cone shape that would tend to automatically orient the tip cap of corn seed down, because the tip cap end of corn seed generally has a smaller cross-sectional area than the crown.

Optionally, a commercially available seed counter tray (custom made for each application from Hoffman Manufacturing Inc., Jefferson, Oreg. USA) could be used to position ninety-six seed 3 in appropriate spaced apart positions and then, in one step, drop all ninety-six simultaneously into individual wells in seed tray 220 of FIG. 3E. Then, drilling can commence sequentially seed by seed in seed tray 220 with debris from each drilled seed automatically, by vacuum, directed to a corresponding sample tray 214 well.

As will be appreciated, this embodiment does not require a vacuum to be pulled as a part of the drill.

This second embodiment relating to drilling can meet at least some of the itemized objectives (a)-(f) similarly to the first embodiment.

3. Options and Alternatives

Variations obvious to those skilled in the art will be included within this description.

For example, any of a number of methods and structures could be used to either adjust drilling depth or control drilling depth. In this embodiment, cone 206 could be spring-loaded such that it is held in an outward position by a spring or springs. When drill 202 is manipulated to bring cone 206 into position around a seed 3 sitting on a surface and then moved downward, cone 206 would pressed against the surface and allow drill 202 and its bit 203 to move downward into seed 3 until cone 206 hits an end stop on drill 202. This would limit the distance bit 203 could drill into seed 3.

Alternative tools might be used to take a sample of a seed. An example would be a small reciprocating saw or carver to take a sliver sample from a seed 3.

The seed 3 could be pre-positioned in spaced apart locations in a matrix of clay or another carrier and then each drilled in position in the carrier, with the debris collected and indexed from each drilling.

The multi-well apparatus described above is configured with ninety six wells, which is a conventional number for many analytical methods practiced by plant scientists. Other well configurations are also contemplated, such as 12, 24, 48 and 384 well models.

E. Fourth Concept

Sand Debris from Individual Seed at Correlated Locations on Sand Paper Sheet, Punch Out and Collect Locations from Sand Paper Sheet

1. Embodiment 1 a) Apparatus (FIGS. 4A-C)

It has been discovered that, at least in some circumstances, a sufficient quantity of sample debris can be removed from a seed 3 by sanding its surface slightly with commercially available sandpaper (e.g. P150 grit 230N sheet sandpaper from, for example, 3M Company, White Bear Lake, Minn. USA). Furthermore, the sandpaper tends to retain the debris on its surface. A spray fixative could optionally be used to further hold the debris on the sandpaper.

The exemplary embodiment of FIGS. 4A-C uses a sheet 600 of sandpaper of a size that can sand and retain debris for a desired number of seed 3. In FIG. 4A, sand paper 600 is illustrated as having sixteen such locations (i.e. Row 1, Column 1; Row 1, Column 2 . . . Row 4, Column 4), but as indicated in FIGS. 4D-F, it is preferred that more samples be simultaneously be taken (i.e. 96). FIGS. 4A-C show 16 positions to illustrate the principles of this embodiment, but it would be applied to 96 positions in this example. However, it is to be understood that sand paper 600 could be sized to have any number of locations, including just one.

Sand paper 600 is fixed by conventional means (e.g. adhesive, hook and loop material, or clamping) onto pad 602 of a conventional, commercially available orbital sander that is inverted. It can be held in the inverted position by a frame or mount (not shown) so that it is stable and rigid.

A punch plate 612 (FIG. 4B) has 96 downward extending punches 610 that correspond with the 96 sample locations of sandpaper 600. The diameter and shape of the distal ends of punches 610 can be sized to punch out pieces of sandpaper 600 that contain a substantial amount (or all of) the debris from a seed at each sample location of sandpaper 600. Two shapes for the distal ends could be oblong or elliptical (approximately 0.5 inches by 0.25 inches). A sample tray 614 of a corresponding number of wells to sandpaper sample locations can be used to catch each of the punched out pieces 601 of sandpaper 600.

b) Operation

(1) Pre-Processing (FIG. 1B)

The only pre-processing of seed 3 is that it be shelled from its ear.

(2) Singulation

As can be appreciated, the worker will manually, with fingers or with a tool such as forceps, pliers, or multi-pronged jewelers tweezers 606 of FIG. 4A, pick up an individual seed 3 and press it down slightly on an appropriate location on sandpaper 600 (see FIG. 4A) while orbital sander motor 604 is running until it leaves a sufficient amount of debris. The worker then would index that seed, pick up the next seed 3, move to the next sandpaper location, and repeat. This would be repeated until all seed 3 have been sampled or the locations of sandpaper 600 used up.

(3) Orientation

The worker would manually manipulate seed 3 to sand off debris from the desired part of seed 3.

(4) Sample Separation

The grit of sandpaper 600 and orbital action of the sander (e.g. ¼" orbital motion, standard router speed controller) would separate fragments or debris from seed 3 and would tend to hold the same in its grit. This would basically produce a small area of debris on the sandpaper separated from seed 3 by the sanding. In FIGS. 4A and B, sandpaper 600 is maintained horizontal so as to deter movement of debris from the appropriate location. Optionally, the sandpaper can be sprayed with a sealant, such as commercial art sealant (for example, Krylon® Workable Fixative), in order to adhere the seed particles more firmly to the sandpaper.

As discussed previously, it is preferable that the amount of the sample debris be sufficient for accurate biochemical, genetic, or phenotypic testing and small enough to minimize the effect on germination potential of seed 3 after the sample is separated.

(5) Collection of Samples

FIG. 4B illustrates that once sample separation is completed by depositing debris from a desired number of seed 3 in appropriate corresponding locations on sandpaper 600, the sandpaper 600 is positioned over a sample tray 614 with corresponding number and spacing of wells to the debris locations on sandpaper 600. Punch plate 612 would be pressed down on sandpaper 600 with punches 610 in appropriate alignment with corresponding locations on sandpaper 600 and wells underneath. As shown in FIG. 4C, punches 610 are configured to punch or cut out small pieces 601 of sandpaper 600 which contain debris from seed 3. The punched out pieces 601 would drop by gravity into appropriate corresponding sample tray wells.

(6) Collection of Cut Seed

The sanded seed 3 could be directed to individual wells in an appropriate seed plate in the same or correlated well position as its corresponding sample in the sample plate.

(7) Post-Processing

Biochemical, genetic, or phenotypic testing of debris can proceed as previously described. The sanded seed correlated to its sample, if selected because it contains desired biochemical, genetic, or phenotypic traits, can then be used accordingly.

The debris can be relatively easily separated from the punched out pieces of sandpaper for analysis.

The embodiments of this fourth concept also balance the variety of issues and factors involved relative to the itemized objectives (a)-(f) of the Background of the Invention.

(a) Viability

Controlled sanding has been shown to not significantly affect the germination potential for the sampled seed and provide a useful amount of sample. By appropriate selection of sandpaper grit and characteristics, and sanding force, range of movement, and other controllable factors of sanding, even relatively small seed can be sampled non-lethally. In the example of corn, the above-mentioned sanding parameters allow sanded debris from the endosperm to be removed non-lethally from the sampled seed. Sanding presents minimal risk of damage to the seed by crushing or tearing.

(b) Sample Amount

Sample amount can be controlled in quantity by control of area and depth of sanding to control amount of seed debris or sample removed. Location of tissue removal from the seed can also be substantially controlled. Sampling can be controlled to reduce risk of removal of too much sample.

(c) Sample Location

Not only size of sample, but sample location can be controlled. As mentioned previously regarding corn seed, sampling from certain seed locations may be undesirable (e.g. from at or near the germ because it can affect viability of the seed). Sanding can be controlled manually or otherwise. The orientation of the sand paper to the seed can be adjusted accordingly. Orientation can assist with this objective. For example, as described with respect to FIG. 4D, a lid or plate (or some other seed holder) could be configured to have a receiver for each seed that facilitates orientation of the seed. Plural seed could be placed in position in such receivers. The lid could then be moved relative to the sandpaper to concurrently sample each seed from substantially the same location because of the relatively consistent orientation (e.g. crown for corn seed) of the seed to the sandpaper.

(d) Throughput

Some versions of this sanding approach are automated to improve throughput of sample collection from plural seed. Although sanding, in one embodiment, is done manually, automation or at least semi-automation of some of the steps improve throughput of sample collection (an example of which is described and shown in the second embodiment). But further, with both described embodiments, handling of samples by punching concurrently pieces of the sandpaper holding plural samples, and moving them to indexed locations, can be quicker than collecting debris from each seed and then manually transferring each sample quantity to a container or well.

(e) Avoiding Contamination

It has been found that the debris (the sample) sanded from the seed tends to be held in place on the sandpaper. This assists to reduce risk of contamination of samples, but also provides a ready-made storage device for samples, at least temporarily. Use of sandpaper characteristics to collect and hold samples reduces contamination risks and improves throughput. Even though sanding can create or disrupt some dust or debris, and the sandpaper would physically abut the seed, collection of the punched-out sandpaper pieces holding the samples is a way to reduce risk of cross-contamination. Cleaning of the punches may be desirable after each sample, but may not be needed or may reduce contamination risk over sample collection methods that do produce or disrupt dust or debris.

(f) Tracking Samples

Substantial automation of handling of samples and sampled seeds can facilitate automated or semi-automated correlation between samples and the seed from which they were sampled, and/or between samples or between seed.

Automated or automatic orientation and segregation and collection of samples and sampled seeds assist with this objective.

The sanding concepts can involve some manual steps. However, they provide a balancing of the itemized objectives to achieve acceptable levels with respect to all those objectives. While they may not achieve levels at or near some of the other concepts for all the itemized objectives, these sanding embodiments are less complex and expensive than some others, and may require less operator training, calibration, and maintenance. Also, as indicated in the sanding embodiments, the sanding concept can take different forms, some of which vary between each other on the itemized objectives. The designer can factor the itemized objectives and other issues and factors into the chosen system according to desire or need.

2. Options and Alternatives

Variations obvious to those skilled in the art will be included within this description.

Optionally, any number of different types of sand paper, sanding surfaces, rough or abrasive surfaces could be incorporated in place of sandpaper 600 described above. Examples include but are not limited to a multitude of sand paper grits (e.g. 40, 80, 150, 240, 400, 600, 1200, 3000) and paper adhesives, grinding stones, steel wool, or files. Abrasive materials that are not conducive to being punched like the sandpaper could be still used to create the seed sample debris. The sample debris could then be collected similarly to the seed drillings described in the third concept of this document.

Additionally there are several options for creating a cut-out or punch of the seed sample debris that have been collected on sandpaper-like materials. Examples include but are not limited to any type of manual or power operated cutting, shearing, punching, or laser etching type of tool.

FIGS. 4D-F illustrate an exemplary embodiment for a ninety-six sample system. The orbital sander 604 could be mounted in collar 622 (see FIG. 4D) which is supported in sound insulated box 620. The electrical cord for sander 604 can extend out of outlet 623. Outlet 623 could be sealed and insulated for sound. As indicated by dashed lines, the head of orbital sander 604 would extend up to around the plane of the opening to box 620 and sandpaper attached to it so that the sandpaper basically fills the opening to box 620 and is in that plane. Hinged lid 624 includes 96 oblong or rectangular openings that form a guide template 626 for the insertion of 96 corn seed, one per opening. Note the shape of the openings is selected to position each of the 96 seed in a similar rotational orientation. Seed can either be interference fit into the openings from the bottom side of lid 624 when hinged up and then the lid pivoted down and pressed down while sander 604 operates to abrade debris from each of the 96 seed into discrete uniformly spaced apart positions on the sandpaper, or the seed can be placed into the openings from the top of lid 624 when closed on box 620 so that the desired portion of each seed extends through lid 624. A flat plate or pad could be pressed onto the top of lid 620 (with the 96 seed in place) and the sander operated to, again, get a sample from each seed in a discrete location on the sand paper. As can be appreciated, by positioning each seed in the same orientation relative the sandpaper, a sample from the same part of 96 seed can be obtained simultaneously.

The lid of box 620 could then be pivoted up and the sandpaper removed from the sander and box 620 and placed in a sandpaper tray 640 (see FIG. 4F). Sandpaper tray 640 is in the base of a hydraulic punch press (see FIG. 4E). A hydraulic ram (not shown) is operatively positioned between mounting plate 632 on press frame 630 and collar 636 on punch plate 612. Punch plate 612 moves down on rails 638, upon actuation of pump 634 for the hydraulic ram so that punches or studs 610 move down and through corresponding punch holes 642 in sandpaper tray 640. The studs 620 are sized to punch out approximately the areas in which samples from the sanding of the seed are deposited. The punched-out areas of the sandpaper, with samples thereon, could fall by gravity directly into corresponding individual wells of a 96 well index tray or plate 59 or 63 (see FIG. 4F).

In this manner, 96 samples could be simultaneously taken from 96 seed and indexed for further use. The ram can be actuated to return punch plate 612 to a raised position to be ready for a next punching operation.

As can be further appreciated, some seed does not need identical orientation for sample-taking. An example is soybean seed. In such cases, careful orientation relative the sandpaper is not required.

F. Summary of Exemplary Embodiments

As can be appreciated by reference to the exemplary embodiments, each represents apparatus and methods designed to facilitate non-lethal quick and accurate collection of tissue samples from corn seed in useful amounts. Some of the concepts disclose not only ways to separate a sample from the seed, but also position and orient the seed automatically prior to taking the sample. But each embodiment provides an aspect that is believed to represent an improvement in at least one form from the state of the art.

G. Options and Alternatives

As can be appreciated by those of ordinary skill in the art, the embodiments of the invention disclosed herein are exemplary only and not comprehensive of the forms they can take. Variations obvious to those skilled in the art will be included within the scope of the invention and its embodiments.

Some examples are set forth below.

1. Apparatus

The size, configuration, and materials for the components of the exemplary embodiments can vary according to need and desire.

2. Methods

The precise method steps can vary according to need and desire.

3. Singulation

Singulation is not limited to the specific examples given. Other apparatus and methods are, of course, possible.

4. Orientation

Iron-based paint and magnets is disclosed as one way to automatically orient seed. This is particularly applicable to corn seed because the paint can be applied while the seed is on the ear, and this automatically results in paint only on the crowns of the seed. Thus, the crown ends of the seed are magnetically attracted into abutment with the magnets, which in turn orients the tip cap to be outward.

As can be appreciated by those skilled in the art, the iron-based paint could be applied in different ways or locations to the seed once they are separated from the ear if a different orientation was desired. However, application when on the ear is quick and convenient for plural seed.

Note, though, that some embodiments allow for adjustable orientation of seed 3 before cutting, although it is not automatic. By "automatic" it is meant acting or operating in a manner essentially independent of external influence or control, or operating without human intervention.

Note also that at least some orientation of seed can be manually accomplished by how they are inserted into, for example, seed plate 220 of FIG. 3E. The geometry of such structures can, in some circumstances help orient a seed. This might be particularly true for seed that has a non-symmetrical but consistent shape. Corn is such an example.

5. Seed Preparation a) Pre-Processing

Iron-based paint is one pre-processing step for the embodiments utilizing automatic seed positioning and orientation with magnets. As discussed elsewhere in this disclosure, the application of electrostatic materials to the seed can be achieved in a variety of ways. It is possible that other substances could be applied to seed to accomplish at least similar functions, in whole or in part. For example, a pressure-sensitive or other non-permanent adhesive could be applied to at least one portion of the seed so that it would adhere to a sampling position in a certain orientation. Another example is use of electrostatic or electrically charged particles as the means to stick high magnetic permeability (such as iron or steel) material (e.g. particles, sheet, or piece(s)) onto the seed. Powder coating is one method.

b) Post-Processing (1) Sealing

Optionally after sample-taking a seed treatment or similar substance could be applied over the area of the seed from which the sample is taken.

For example a substance such as paraffin could be placed or coated over the cut, drilled area, or sanded area of cut seed 60. There are also commercially available grain sealers that might be used (e.g. Log-Gevity™ product from ABR Products, Inc., Franklin, Wis. USA) to protect against intrusion into the cut seed 60.

Another example would be to use a seed treatment such as Lockout™ (Becker Underwood Inc.) in order to protect nutrients from eroding from the seed.

(2) Agents

Optionally, one or more substances could be applied to the seed after sampling. Examples include, but are not limited to, insecticides, fertilizers or growth enhancers, or anti-fungal agents.

One specific example is bentonite, which is a natural substance that has anti-fungal characteristics. Such substances could be used to increase germination potential and reduce pathogenic attacks on the cut seed 60. Commercially available chemical seed treatment fungicides include Captan™, a broad-spectrum fungicide, from Drexel Chemical Co., Memphis, Tenn. USA; and Apron™ (metalaxyl) and Maxim™ (fludioxonil) fungicides, from Syngenta, Greensboro, N.C. USA.

6. Analytical Techniques

As can be appreciated by those skilled in the art, the methods by which the samples are processed to derive biochemical, genetic, or phenotypic information can include almost any known in the art method. Many are well-documented and widely known.

7. Applications a) Type of Seed

The exemplary embodiments and the invention are not limited to corn seed, but can be applied to virtually any seed. Soybeans are but one example. Canola is another example.

b) Uses

Embodiments of the invention can be used in a wide variety of laboratory assays and protocols, and can be applied to various aspects of plant research. Some, but not all, of the ways the invention could be applied, include DNA and RNA extraction and testing procedures, genotyping, seed sorting for transgenic seed versus non-transgenic seed, identification of markers, testing for adventitious presence, spectroscopy, food research, oil chemistry and protein biochemistry. This is but a sampling of the methods where the embodiments of the invention find use, and is not intended to be limiting in any way.

What is claimed is:

1. A method of sampling seed comprising:
   applying a magnetic substance to a particular location on a seed corresponding to a desired pre-determined orientation of the seed;
   automatically positioning the seed in the pre-determined orientation by influence of a magnetic field;
   removing a measurable sample from the seed.

2. The method of claim 1, wherein the removal of the measurable sample from the seed while in the pre-determined orientation does not cause a significant reduction to germination potential of the seed.

3. The method of claim 1 wherein the step of automatically positioning the seed in a pre-determined orientation comprises:
   magnetically attracting the magnetically active substance in a manner related to the pre-determined orientation.

4. The method of claim 1 wherein the seed is corn seed.

5. The method of claim 3 wherein the seed is corn seed and the particular location on the seed is the crown of the seed.

6. The method of claim 1 further comprising automatically positioning a plurality of seed in the pre-determined orientation for high throughput processing of plural seed by influence of the magnetic field.

7. A method of sampling seed comprising:
   applying a magnetically active substance to a particular location on a seed corresponding to a desired pre-determined orientation of the seed;
   magnetically attracting the magnetically active substance on the seed to automatically position the seed in the desired pre-determined orientation; and
   removing a measurable sample from the seed while being retained in the desired pre-determined orientation.

8. The method claim 7 wherein the particular location on the seed where the magnetically active substance is applied is a single location on the seed independent of other locations on the seed.

9. The method of claim 8 wherein placement of the magnetically active substance at the single location on the seed is based on the desired orientation and position of the seed for facilitating sampling.

10. The method of claim 7 wherein the particular location on the seed corresponding with the desired pre-determined orientation is the crown of the seed.

11. The method of claim 7 wherein the magnetically active substance is applied before removing a measurable sample from the seed.

12. The method of claim 7 wherein the pre-determined orientation of the seed corresponds with the step of removing a measurable sample from the seed.

13. The method of claim 7 wherein the magnetically attracting step comprises subjecting the magnetically active substance to the influence of a magnetic field for automatically orienting the seed in the desired pre-determined orientation.

14. A method of sampling seed comprising:
- identifying a single location on a seed corresponding to a pre-determined orientation of the seed for facilitating sampling;
- applying a magnetically active substance to the single location on the seed before sampling;
- subjecting the seed to influence of a magnetic field at a position corresponding with the step of sampling;
- attracting the magnetically active substance to automatically position and orient the seed in the pre-determined orientation; and
- removing a measurable sample from the seed.

15. The method of claim 14 wherein the single location on the seed corresponding with the desired pre-determined orientation is the crown of the seed.

16. The method of claim 14 wherein the single location on the seed where the magnetically active substance is applied is independent of other locations on the seed to allow orienting and positioning of the seed to correspond with the pre-determined orientation.

17. The method of claim 14 wherein the pre-determined orientation of the seed resulting from placement the magnetically active substance corresponds with a location on the seed suited for facilitating removal of the measurable sample.

* * * * *